(12) United States Patent
Williams et al.

(10) Patent No.: US 11,857,275 B2
(45) Date of Patent: Jan. 2, 2024

(54) SYSTEMS AND METHODS FOR TARGETED NEUROMODULATION

(71) Applicant: The Board of Trustees of the Leland Stanford Junior University, Stanford, CA (US)

(72) Inventors: Nolan R. Williams, Half Moon Bay, CA (US); Adi Maron-Katz, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/499,781

(22) Filed: Oct. 12, 2021

(65) Prior Publication Data

US 2022/0110694 A1    Apr. 14, 2022

Related U.S. Application Data

(60) Provisional application No. 63/090,680, filed on Oct. 12, 2020.

(51) Int. Cl.
*G01R 33/48* (2006.01)
*A61B 34/20* (2016.01)
(Continued)

(52) U.S. Cl.
CPC ............ *A61B 34/20* (2016.02); *A61B 5/0036* (2018.08); *A61B 5/055* (2013.01); *A61N 1/20* (2013.01);
(Continued)

(58) Field of Classification Search
CPC ....... A61B 34/20; A61B 5/0036; A61B 5/055; A61N 1/20; A61N 1/36096; A61N 2/006; G01R 33/4806; G01R 33/5608
See application file for complete search history.

(56) References Cited

U.S. PATENT DOCUMENTS 10,449,384 B2    10/2019  Williams et al.
10,595,735 B2    3/2020   Williams et al.
(Continued)

FOREIGN PATENT DOCUMENTS

BR    1120230068380 A2    6/2023
EP           3737467 A2    11/2020
(Continued)

OTHER PUBLICATIONS

Mencarelli et al. "Network Mapping of Connectivity Alterations in Disorder of Consciousness: Towards Targeted Neuromodulation", Published Online Mar. 18, 2020, J. Clin. Med (Year: 2020).*
(Continued)

*Primary Examiner* — Christopher L Cook
(74) *Attorney, Agent, or Firm* — KPPB LLP

(57) ABSTRACT

Systems and methods for neuronavigation in accordance with embodiments of the invention are illustrated. Targeting systems and methods as described herein can generate personalized stimulation targets for the treatment of mental conditions. In many embodiments, direct stimulation of a personalized the stimulation target indirectly impacts a brain structure that is more difficult to reach via the stimulation modality. In various embodiments, the mental condition is major depressive disorder. In a number of embodiments, the mental condition is suicidal ideation.

22 Claims, 6 Drawing Sheets

(51) Int. Cl.

| | |
|---|---|
| *A61B 5/00* | (2006.01) |
| *A61B 5/055* | (2006.01) |
| *G01R 33/56* | (2006.01) |
| *A61N 2/00* | (2006.01) |
| *A61N 1/20* | (2006.01) |
| *A61N 1/36* | (2006.01) |

(52) U.S. Cl.
  CPC ......... *A61N 1/36096* (2013.01); *A61N 2/006* (2013.01); *G01R 33/4806* (2013.01); *G01R 33/5608* (2013.01)

(56) References Cited

U.S. PATENT DOCUMENTS

| | | | |
|---|---|---|---|
| 11,013,423 | B2 | 5/2021 | Williams et al. |
| 11,213,215 | B2 | 1/2022 | Williams et al. |
| 2002/0058867 | A1 | 5/2002 | Breiter et al. |
| 2006/0217781 | A1 | 9/2006 | John |
| 2007/0173901 | A1 | 7/2007 | Reeve |
| 2009/0105521 | A1 | 4/2009 | Bentwich |
| 2011/0224571 | A1 | 9/2011 | Pascual-leone et al. |
| 2011/0245633 | A1 | 10/2011 | Goldberg et al. |
| 2014/0058279 | A1 | 2/2014 | Shinba |
| 2014/0206945 | A1 | 7/2014 | Liao |
| 2015/0119689 | A1 | 4/2015 | Pascual-leone et al. |
| 2015/0272493 | A1* | 10/2015 | Liu .................. A61B 5/055 600/410 |
| 2016/0008620 | A1 | 1/2016 | Stubbeman |
| 2016/0019693 | A1 | 1/2016 | Silbersweig et al. |
| 2016/0292859 | A1* | 10/2016 | Magda .................. G06T 7/149 |
| 2016/0367804 | A1 | 12/2016 | Peng et al. |
| 2017/0249438 | A1 | 8/2017 | Jain et al. |
| 2019/0090749 | A1* | 3/2019 | Leuthardt ............ G06T 7/0012 |
| 2019/0216342 | A1* | 7/2019 | Williams ............... A61B 5/165 |
| 2019/0217112 | A1 | 7/2019 | Williams et al. |
| 2019/0217113 | A1 | 7/2019 | Williams et al. |
| 2019/0217116 | A1 | 7/2019 | Williams et al. |
| 2019/0336018 | A1 | 11/2019 | Williams et al. |
| 2020/0214581 | A1 | 7/2020 | Williams et al. |
| 2021/0353224 | A1 | 11/2021 | Etkin et al. |
| 2021/0378531 | A1 | 12/2021 | Williams et al. |
| 2022/0139530 | A1* | 5/2022 | Kollada ................ A61B 5/055 705/2 |
| 2022/0202302 | A1 | 6/2022 | Williams et al. |

FOREIGN PATENT DOCUMENTS

| | | | |
|---|---|---|---|
| EP | 4210819 | A1 | 7/2023 |
| GB | 2585282 | A | 1/2021 |
| GB | 2614504 | A | 7/2023 |
| JP | 2021510572 | A | 4/2021 |
| WO | 2017172487 | A1 | 10/2017 |
| WO | 2019140303 | A2 | 7/2019 |
| WO | 2019140303 | A3 | 7/2019 |
| WO | 2022081611 | A1 | 4/2022 |

OTHER PUBLICATIONS

Kammer et al., "Transcranial magnetic stimulation in the visual system. I. The psychophysics of visual suppression", Experimental Brain Research, vol. 160, No. 1, Jan. 2005, pp. 118-128.
Kim et al., "Inhibitory control of excitable dendrites in neocortex", Journal of Neurophysiology, vol. 74, No. 4, Oct. 1995, pp. 1810-1814.
Kimbrell et al., "Regional Cerebral Glucose Utilization in Patients with a Range of Severities of Unipolar Depression", Biological Psychiatry, vol. 51, No. 3, Feb. 1, 2002, pp. 237-252.
Klomjai et al., "Basic Principles of Transcranial Magnetic Stimulation (TMS) and Repetitive TMS (rTMS)", Annals of Physical and Rehabilitation Medicine, Sep. 1, 2015, vol. 58, Issue No. 4, p. 208-213.
Kobayashi et al., "Ipsilateral motor cortex activation on functional magnetic resonance imaging during unilateral hand movements is related to interhemispheric interactions", NeuroImage, vol. 20, No. 4, Dec. 2003, pp. 2259-2270.
Kozel et al., "How Coil-Cortex Distance Relates to Age, Motor Threshold, and Antidepressant Response to Repetitive Transcranial Magnetic Stimulation", Journal of Neuropsychiatry and Clinical Neurosciences, vol. 12, No. 3, Aug. 2000, pp. 376-384.
Kramár et al., "Synaptic evidence for the efficacy of spaced learning", Proceedings of the National Academy of Sciences, vol. 109, No. 13, Mar. 27, 2012, pp. 5121-5126.
Kujirai et al., "Corticocortical inhibition in human motor cortex", Journal of Physiology, vol. 471, No. 1, Nov. 1, 1993, pp. 501-519.
Larkum, "A cellular mechanism for cortical associations: an organizing principle for the cerebral cortex", Trends in Neurosciences, vol. 36, No. 3, Mar. 2013, pp. 141-151.
Larkum et al., "A new cellular mechanism for coupling inputs arriving at different cortical layers", Nature, vol. 398, Mar. 25, 1999, pp. 338-341.
Larkum et al., "Synaptic Integration in Tuft Dendrites of Layer 5 Pyramidal Neurons: A New Unifying Principle", Science, vol. 325, No. 5941, Aug. 7, 2009, pp. 756-760.
Larson et al., "Induction of Synaptic Potentiation in Hippocampus by Patterned Stimulation Involves Two Events", Science, vol. 232, No. 4753, May 23, 1986, pp. 985-988.
Lavzin et al., "Nonlinear dendritic processing determines angular tuning of barrel cortex neurons in vivo", Nature, vol. 490, Oct. 18, 2012, pp. 397-401.
Lee et al., "Acute Remapping within the Motor System Induced by Low-Frequency Repetitive Transcranial Magnetic Stimulation", The Journal of Neuroscience, vol. 23, No. 12, Jun. 15, 2003, pp. 5308-5318.
Lee et al., "Canonical Organization of Layer 1 Neuron-Led Cortical Inhibitory and Disinhibitory Interneuronal Circuits", Cerebral Cortex, vol. 25, No. 8, Aug. 2015, Electronic Publication: Feb. 18, 2014, pp. 2114-2126.
Lee et al., "The effects of inhibitory and facilitatory intracortical circuits on interhemispheric inhibition in the human motor cortex", The Journal of Physiology, vol. 580, Pt. 3, May 1, 2007, Published Online: Feb. 15, 2007, pp. 1021-1032.
Lehrer et al., "Heart rate variability biofeedback: how and why does it work?", Frontiers in Psychology, vol. 5, No. 756, Jul. 21, 2014, pp. 1-9.
Lemogne et al., "Self-referential processing and the prefrontal cortex over the course of depression: A pilot study", Journal of Affective Disorders, vol. 124, No. 1-2, Jul. 2010, pp. 196-201.
Levinson et al., "Evidence of Cortical Inhibitory Deficits in Major Depressive Disorder", Biological Psychiatry, vol. 67, No. 5, Mar. 1, 2010, pp. 458-464.
Li et al., "Antidepressant mechanism of add-on repetitive transcranial magnetic stimulation in medication-resistant depression using cerebral glucose metabolism", Journal of Affective Disorders, vol. 127, No. 1-3, Dec. 2010, pp. 219-229.
Li et al., "Efficacy of prefrontal theta-burst stimulation in refractory depression: a randomized sham-controlled study", Brain: A Journal of Neurology, vol. 137, May 10, 2014, pp. 2088-2098.
Li et al., "Impaired Prefronto-Thalamic Functional Connectivity as a Key Feature of Treatment-Resistant Depression: A Combined MEG, PET and rTMS Study", PLOS One, vol. 8, No. 8, Aug. 2, 2013, 8 pgs.
Li et al., "Major Depressive Disorder and Stroke Risks: A 9-Year Follow-Up Population-Based, Matched Cohort Study", PLOS One, vol. 7, No. 10, Oct. 8, 2012, 9 pgs.
Li et al., "Structural and cognitive deficits in remitting and non-remitting recurrent depression: A voxel-based morphometric study", NeuroImage, vol. 50, No. 1, Mar. 2010, pp. 347-356.
Lisanby et al., "Daily Left Prefrontal Repetitive Transcranial Magnetic Stimulation in the Acute Treatment of Major Depression: Clinical Predictors of Outcome in a Multisite, Randomized Controlled Clinical Trial", Neuropsychopharmacology, vol. 34, No. 2, Jan. 2009, Electronic Publication: Aug. 13, 2008, pp. 522-534.

(56) References Cited

OTHER PUBLICATIONS

Liu et al., "Role of NMDA Receptor Subtypes in Governing the Direction of Hippocampal Synaptic Plasticity", Science, vol. 304, No. 5673, May 14, 2004, pp. 1021-1024.
Losonczy et al., "Integrative Properties of Radial Oblique Dendrites in Hippocampal CA1 Pyramidal Neurons", Neuron, vol. 50, No. 2, Apr. 20, 2006, pp. 291-307.
Lovett-Barron et al., "Behavioral consequences of GABAergic neuronal diversity", Current Opinion in Neurobiology, vol. 26, Jun. 2014, pp. 27-33.
Lynch et al., "Differences Between Synaptic Plasticity Thresholds Result in New Timing Rules for Maximizing Long-Term Potentiation", Neuropharmacology, vol. 61, No. 1, Jan. 2013, pp. 27-36.
Maeda et al., "Interindividual variability of the modulatory effects of repetitive transcranial magnetic stimulation on cortical excitability", Experimental Brain Research, vol. 133, No. 4, Aug. 2000, pp. 425-430.
Maron-Katz et al., "Individual Patterns of Abnormality in Resting-State Functional Connectivity Reveal Two Data-Driven PTSD Subgroups", American Journal of Psychiatry, published online: Dec. 16, 2019, 29 pgs.
Martin et al., "Repetitive transcranial magnetic stimulation for the treatment of depression: Systematic review and meta-analysis", British Journal of Psychiatry, vol. 182, Jun. 2003, pp. 480-491.
McDonald et al., "Improving the antidepressant efficacy of transcranial magnetic stimulation: Maximizing the number of stimulation and treatment location in treatment resistant depression", Depression & Anxiety, vol. 28, No. 11, Nov. 2011, published online Sep. 2, 2011, pp. 973-980.
Modirrousta et al., "Efficacy of twice-daily vs once-daily sessions of repetitive transcranial magnetic stimulation in the treatment of major depressive disorder: a retrospective study", Neuropsychiatric Disease and Treatment, vol. 14, Dec. 7, 2017, pp. 309-316.
Muellbacher et al., "Effects of low-frequency transcranial magnetic stimulation on motor excitability and basic motor behavior", Clinical Neurophysiology, vol. 111, No. 6, Jun. 1, 2000, pp. 1002-1007.
Mueller et al., "Simultaneous transcranial magnetic stimulation and single-neuron recording in alert non-human primates", Nature Neuroscience, vol. 17, No. 8, Aug. 2014, Electronic Publication: Jun. 29, 2014, pp. 1130-1136.
Murayama et al., "Dendritic encoding of sensory stimuli controlled by deep cortical interneurons", Nature, vol. 457, No. 7233, Feb. 26, 2009, Electronic Publication: Jan. 18, 2009, pp. 1137-1141.
Murayama et al., "Fiberoptic System for Recording Dendritic Calcium Signals in Layer 5 Neocortical Pyramidal Cells in Freely Moving Rats", Journal of Neurophysiology, vol. 98, No. 3, Sep. 2007, pp. 1791-1805.
Murd et al., "Repetitive TMS over V5/MT shortens the duration of spatially localized motion aftereffect: The effects of pulse intensity and stimulation hemisphere", Vision Research, vol. 68, Sep. 1, 2012, pp. 59-64.
Murphy et al., "Transcranial magnetic stimulation (TMS) inhibits cortical dendrites", ELife, vol. 5, Mar. 18, 2016, 12 pgs.
Nettekoven et al., "Dose-Dependent Effects of Theta Burst rTMS on Cortical Excitability and Resting-State Connectivity of the Human Motor System", Journal of Neuroscience, vol. 34, No. 20, May 14, 2014, pp. 6849-6859.
Nettekoven et al., "Inter-individual variability in cortical excitability and motor network connectivity following multiple blocks of rTMS", NeuroImage, vol. 118, Sep. 2015, Electronic Publication: Jun. 5, 2015, pp. 209-218.
Nishiyama et al., "Calcium stores regulate the polarity and input specificity of synaptic modification", Nature, vol. 408, No. 6812, Nov. 30, 2000, pp. 584-588.
Nitsche et al., "Excitability changes induced in the human motor cortex by weak transcranial direct current stimulation", Journal of Physiology, vol. 527, Pt. 3, Sep. 15, 2000, pp. 633-639.
Nyffeler et al., "Extending lifetime of plastic changes in the human brain", European Journal of Neuroscience, vol. 24, No. 10, Nov. 2006, pp. 2961-2966.
Nyffeler et al., "One Session of Repeated Parietal Theta Burst Stimulation Trains Induces Long-Lasting Improvement of Visual Neglect", Stroke, vol. 40, No. 8, Jun. 11, 2009, pp. 2791-2796.
Oathes et al., "Individualized non-invasive brain stimulation engages the subgenual anterior cingulate and amygdala", bioRxiv, Dec. 21, 2018, 35 pgs.
Ogiue-Ikeda et al., "The effect of repetitive transcranial magnetic stimulation on long-term potentiation in rat hippocampus depends on stimulus intensity", Brain Research, vol. 993, No. 1-2, Dec. 12, 2003, pp. 222-226.
Olah et al., "Output of neurogliaform cells to various neuron types in the human and rat cerebral cortex", Frontiers in Neural Circuits, vol. 1, No. 4, Nov. 2007, 7 pgs.
Olah et al., "Regulation of cortical microcircuits by unitary GABA-mediated volume transmission", Nature, vol. 461, No. 7268, Oct. 29, 2009, pp. 1278-1281.
O'Reardon et al., "Efficacy and Safety of Transcranial Magnetic Stimulation in the Acute Treatment of Major Depression: A Multisite Randomized Controlled Trial", Biological Psychiatry, vol. 62, No. 11, Dec. 1, 2007, pp. 1208-1216.
Palmer et al., "Inhibitory regulation of dendritic activity in vivo", Frontiers in Neural Circuits, vol. 6, No. 26, May 2012, 10 pgs.
Palmer et al., "The Cellular Basis of GABAB-Mediated Interhemispheric Inhibition", Science, vol. 335, No. 6071, Feb. 24, 2012, pp. 989-993.
Pascual-Leone et al., "Fast Backprojections from the Motion to the Primary Visual Area Necessary for Visual Awareness", Science, vol. 292, No. 5516, Apr. 20, 2001, pp. 510-512.
Pashut et al., "Mechanisms of Magnetic Stimulation of Central Nervous System Neurons", PLOS Computational Biology, vol. 7, No. 3, Mar. 24, 2011, 18 pgs.
Dumas et al., "[Repetitive transcranial magnetic stimulation in major depression: response factor].", Encephale, vol. 38, No. 4, Sep. 2012, Electronic Publication: Oct. 11, 2011, pp. 360-368.
Dunlop et al., "Functional Connectivity of the Subcallosal Cingulate Cortex and Differential Outcomes to Treatment with Cognitive-Behavioral Therapy of Antidepressant Medication for Major Depressive Disorder", Am. J. Psychiatry, Jun. 1, 2017, vol. 174, No. 6, pp. 533-545.
Duprat et al., "Accelerated Intermittent Theta Burst Stimulation Treatment in Medication-Resistant Major Depression: A Fast Road to Remission?", Journal of Affective Disorders, Aug. 2016, vol. 200, pp. 6-14. Electronic Publication: Apr. 19, 2016.
Eldaief et al., "Transcranial magnetic stimulation in neurology: A review of established and prospective applications", Neurology: Clinical Practice, vol. 3, No. 6, Dec. 2013, pp. 519-526.
Eldaief et al., "Transcranial magnetic stimulation modulates the brain's intrinsic activity in a frequency-dependent manner", Proceedings of the National Academy of Sciences, vol. 108, No. 52, Dec. 27, 2011, pp. 21229-21234.
Evers et al., "The impact of transcranial magnetic stimulation on cognitive processing: an event-related potential study", NeuroReport, vol. 12, No. 13, Sep. 17, 2001, pp. 2915-2918.
Fekadu et al., "A Multidimensional Tool to Quantify Treatment Resistance in Depression: The Maudsley Staging Method", Journal of Clinical Psychiatry, vol. 70, No. 2, Jan. 27, 2009, pp. 177-184.
Fekadu et al., "The Maudsley Staging Method for Treatment-Resistant Depression: Prediction of Longer-Term Outcome and Persistence of Symptoms", Journal of Clinical Psychiatry, vol. 70, No. 7, Jul. 2009, Electronic Publication: May 19, 2009, pp. 952-957.
Ferbert et al., "Interhemispheric Inhibition of the Human Motor Cortex", Journal of Physiology, vol. 453, 1992, pp. 525-546.
Fitzgerald et al., "The effects of repetitive transcranial magnetic stimulation in the treatment of depression", Expert Review of Medical Devices, vol. 8, No. 1, Jan. 2011, pp. 85-95.
Fox, "113. Brain Lesions Associated With Depression are Characterized by a Unique Pattern of Brain Connectivity", Biological Psychiatry, vol. 83, No. 9, Supplement, May 1, 2018, pp. S46-S47.
Fox, "Mapping Symptoms to Brain Networks with the Human Connectome", The New England Journal of Medicine, vol. 379, No. 23, Dec. 6, 2018, pp. 2237-2245.

(56) References Cited

OTHER PUBLICATIONS

Fox et al., "Efficacy of Transcranial Magnetic Stimulation Targets for Depression Is Related to Intrinsic Functional Connectivity with the Subgenual Cingulate", Biol. Psychiatry, 2012, vol. 72, pp. 595-603.
Fox et al., "Measuring and manipulating brain connectivity with resting state functional connectivity magnetic resonance imaging (fcMRI) and transcranial magnetic stimulation (TMS)", NeuroImage, vol. 62, No. 4, Oct. 1, 2012, pp. 2232-2243.
Fox et al., "Resting-state networks link invasive and noninvasive brain stimulation across diverse psychiatric and neurological diseases", Proc Natl Acad Sci, vol. 111, No. 41, Oct. 2014, pp. E4367-E4375.
Fregni et al., "Predictors of antidepressant response in clinical trials of transcranial magnetic stimulation", International Journal of Neuropsychopharmacology, vol. 9, No. 6, Dec. 2006, Electronic Publication: Nov. 23, 2005, pp. 641-654.
Fregni et al., "Technology Insight: noninvasive brain stimulation in neurology—perspectives on the therapeutic potential of rTMS and tDCS", Nature Clinical Practice Neurology, vol. 3, No. 7, Jul. 2007, pp. 383-393.
Froc et al., "Long-Term Depression and Depotentiation in the Sensorimotor Cortex of the Freely Moving Rat", The Journal of Neuroscience, vol. 20, No. 1, Jan. 1, 2000, pp. 438-445.
Gamboa et al., "Impact of repetitive theta burst stimulation on motor cortex excitability", Brain Stimulation, vol. 4, No. 3, Jul. 2011, pp. 141-151, doi: https://doi.org/10.1016/j.brs.2010.09.008.
Gamboa et al., "Simply longer is not better: reversal of theta burst after-effect with prolonged stimulation", Experimental Brain Research, vol. 204, No. 2, Jul. 2010, Electronic Publication: Jun. 22, 2010, pp. 181-187.
George et al., "A two-site pilot randomized 3 day trial of high dose left prefrontal repetitive transcranial magnetic stimulation (rTMS) for suicidal inpatients", Brain Stimul, vol. 7, No. 3, 2014, pp. 421-431.
George et al., "Daily Left Prefrontal Transcranial Magnetic Stimulation Therapy for Major Depressive Disorder: A Sham-Controlled Randomized Trial", Archives Of General Psychiatry, vol. 67, No. 5, May 2010, pp. 507-516.
George et al., "Daily repetitive transcranial magnetic stimulation (rTMS) improves mood in depression", An International Journal for the Rapid Communication of Research in Neuroscience, vol. 6, No. 14, Oct. 2, 1995, pp. 1853-1856.
George et al., "The expanding evidence base for rTMS treatment of depression", Current Opinion in Psychiatry, vol. 26, No. 1, Jan. 2013, pp. 13-18.
Giesel et al., "Improvement of auditory hallucinations and reduction of primary auditory area's activation following TMS", European Journal of Radiology, vol. 81, No. 6, Jun. 2012, pp. 1273-1275.
Goldsworthy et al., "A comparison of two different continuous theta burst stimulation paradigms applied to the human primary motor cortex", Clinical Neurophysiology, 123, 2012, pp. 2256-2263.
Goldsworthy et al., "Neuroplastic Modulation of Inhibitory Motor Cortical Networks by Spaced Theta Burst Stimulation Protocols", Brain Stimulation, vol. 6, No. 3, May 2013, pp. 340-345.
Goldsworthy et al., "Spaced Noninvasive Brain Stimulation: Prospects for Inducing Long-Lasting Human Cortical Plasticity", Neurorehabilitation and Neural Repair, vol. 29, No. 8, Dec. 11, 2014, pp. 714-721.
Goldsworthy et al., "The application of spaced theta burst protocols induces long-lasting neuroplastic changes in the human motor cortex", European Journal of Neuroscience, vol. 35, No. 1, Nov. 25, 2011, pp. 125-134.
Gratton et al., "The effect of theta-burst TMS on cognitive control networks measured with resting state fMRI", Frontiers in Systems Neuroscience, vol. 7, No. 124, Dec. 2013, 14 pgs.
Greenberg et al., "The Economic Burden of Depression in the United States: How Did It Change Between 1990 and 2000?", Journal of Clinical Psychiatry, vol. 64, No. 12, Dec. 2003, pp. 1465-1475.

Hadland et al., "Interference with Performance of a Response Selection Task that has no Working Memory Component: An rTMS Comparison of the Dorsolateral Prefrontal and Medial Frontal Cortex", Journal of Cognitive Neuroscience, vol. 13, No. 8, Nov. 15, 2001, pp. 1097-1108.
Hadley et al., "Safety, tolerability, and effectiveness of high doses of adjunctive daily left prefrontal repetitive transcranial magnetic stimulation for treatment-resistant depression in a clinical setting", J ECT, vol. 27, No. 1, Mar. 2011, pp. 18-25.
Hamilton, "Development of a rating scale for primary depressive illness", The British Journal of Social and Clinical Psychology, vol. 6, No. 4, Dec. 1967, pp. 278-296.
Hanajima et al., "Paired-pulse magnetic stimulation of the human motor cortex: differences among I waves", Journal of Physiology, vol. 509, No. 2, Jun. 1998, pp. 607-618.
Harris et al., "Dendritic Spines: Cellular Specializations Imparting Both Stability and Flexibility to Synaptic Function", Annual Review of Neuroscience, vol. 17, Mar. 1994, pp. 341-371.
Hausmann et al., "No benefit derived from repetitive transcranial magnetic stimulation in depression: a prospective, single centre, randomised, double blind, sham controlled "add on" trial", Journal of Neurology, Neurosurgery, and Psychiatry, vol. 75, No. 2, Feb. 2004, pp. 320-322.
Hawco et al., "Spread of activity following TMS is related to intrinsic resting connectivity to the salience network: A concurrent TMS-fMRI study", Cortex, vol. 108, Nov. 2018, pp. 160-172.
Herwig et al., "Antidepressant effects of augmentative transcranial magnetic stimulation: Randomised multicentre trial", British Journal of Psychiatry, vol. 191, Nov. 2007, pp. 441-448.
Herwig et al., "Transcranial Magnetic Stimulation in Therapy Studies: Examination of the Reliability of "Standard" Coil Positioning by Neuronavigation", Biological Psychiatry, vol. 50, No. 1, Jul. 1, 2001, pp. 58-61.
Hess et al., "Conditions for the induction of long-term potentiation in layer II/III horizontal connections of the rat motor cortex", Journal of Neurophysiology, vol. 75, No. 5, May 1996, pp. 1765-1778.
Hess et al., "Long-term potentiation and long-term depression of horizontal connections in rat motor cortex", Acta Neurobiologiae Experimentalis Journal, vol. 56, No. 1, 1996, pp. 397-405.
Heusler et al., "A repetitive intracortical microstimulation pattern induces long-lasting synaptic depression in brain slices of the rat primary somatosensory cortex", Experimental Brain Research, vol. 135, No. 3, Dec. 2000, pp. 300-310.
Heynen et al., "Long-Term Potentiation of Thalamocortical Transmission in the Adult Visual Cortex In Vivo", The Journal of Neuroscience, vol. 21, No. 24, Dec. 15, 2001, pp. 9801-9813.
Hirsch et al., "Use-dependent changes in synaptic efficacy in rat prefrontal neurons in vitro", Journal of Physiology, vol. 427, No. 1, Aug. 1, 1990, pp. 31-49.
Holtzheimer III et al., "Accelerated repetitive transcranial magnetic stimulation for treatment-resistant depression", Depression & Anxiety, vol. 27, No. 10, Oct. 2010, pp. 960-963.
Huang et al., "The effect of short-duration bursts of high-frequency, low-intensity transcranial magnetic stimulation on the human motor cortex", Clinical Neurophysiology, vol. 115, No. 5, May 2004, pp. 1069-1075.
Huang et al., "The theoretical model of theta burst form of repetitive transcranial magnetic stimulation", Clinical Neurophysiology, vol. 122, No. 5, May 2011, pp. 1011-1018.
Huang et al., "Theta Burst Stimulation of the Human Motor Cortex", Neuron, vol. 45, No. 2, Jan. 20, 2005, pp. 201-206.
Huemmeke et al., "Metabotropic glutamate receptors mediate expression of LTP in slices of rat visual cortex", European Journal of Neuroscience, vol. 15, No. 10, May 2002, pp. 1641-1645.
Hung et al., "Visual Selection and the Human Frontal Eye Fields: Effects of Frontal Transcranial Magnetic Stimulation on Partial Report Analyzed by Bundesen's Theory of Visual Attention", The Journal of Neuroscience, vol. 31, No. 44, Nov. 2, 2011, p. 15904-15913.
Jiang et al., "The organization of two new cortical interneuronal circuits", Nature Neuroscience, vol. 16, No. 2, Feb. 2013, Electronic Publication: Jan. 13, 2013, pp. 210-218.

(56) References Cited

OTHER PUBLICATIONS

Juan et al., "Feedback to V1: a reverse hierarchy in vision", Experimental Brain Research, vol. 150, No. 2, Apr. 8, 2003, pp. 259-263.
Kadvany, "Through Stanford brain research, the depressed feel 'whole' again", Palo Alto Online, Oct. 27, 2017, retrieved from: https://paloaltoonline.com/news/print/2017/10/27/becomingwholeagain on Jan. 8, 2018, 5 pgs.
Pashut et al., "Patch-clamp recordings of rat neurons from acute brain slices of the somatosensory cortex during magnetic stimulation", Frontiers in Cellular Neuroscience, vol. 8, No. 145, Jun. 2014, 12 pgs.
Peinemann et al., "Long-lasting increase in corticospinal excitability after 1800 pulses of subthreshold 5 Hz repetitive TMS to the primary motor cortex", Clinical Neurophysiology, vol. 115, No. 7, Jul. 2004, pp. 1519-1526.
Perellon-Alfonso et al., "Similar effect of intermittent theta burst and sham stimulation on corticospinal excitability: A 5-day repeated sessions study", European Journal of Neuroscience, vol. 48, No. 4, Aug. 2018, pp. 1990-2000.
Perez-Garci et al., "Inhibition of dendritic Ca2+ spikes by GABAB receptors in cortical pyramidal neurons is mediated by a direct Gi/o-βγ-subunit interaction with Cav1 channels", Journal of Physiology, vol. 591, No. 7, Apr. 2013, pp. 1599-1612.
Perez-Garci et al., "The GABAB1b Isoform Mediates Long-Lasting Inhibition of Dendritic Ca2+ Spikes in Layer 5 Somatosensory Pyramidal Neurons", Neuron, vol. 50, May 18, 2006, pp. 603-616.
Plewnia et al., "Treatment of major depression with bilateral theta burst stimulation: A randomized controlled pilot trial", Journal of Affective Disorders, vol. 156, Mar. 1, 2014, pp. 219-223.
Polsky et al., "Computational subunits in thin dendrites of pyramidal cells", Nature Neuroscience, vol. 7, No. 6, May 23, 2004, pp. 621-627.
Reis et al., "Topiramate Selectively Decreases Intracortical Excitability in Human Motor Cortex", Epilepsia, vol. 43, No. 10, Oct. 2002, pp. 1149-1156.
Ridding et al., "Changes in motor cortical excitability induced by paired associative stimulation", Clinical Neurophysiology, vol. 114, No. 8, Aug. 2003, pp. 1437-1444.
Rossi et al., "Safety, ethical considerations, and application guidelines for the use of transcranial magnetic stimulation in clinical practice and research", Clinical Neurophysiology, vol. 120, No. 12, Dec. 2009, pp. 2008-2039.
Ruchsow et al., "Electrophysiological evidence for reduced inhibitory control in depressed patients in partial remission: A Go/Nogo study", International Journal of Psychophysiology, vol. 68, No. 3, Jun. 2008, pp. 209-218.
Ruhe et al., "Staging methods for treatment resistant depression. A systematic review.", Journal of Affective Disorders, vol. 137, No. 1-3, Mar. 2012, pp. 35-45.
Rush, "Limitations in Efficacy of Antidepressant Monotherapy", Journal of Clinical Psychiatry, vol. 68, Suppl. 10, 2007, pp. 8-10.
Samson et al., "Brain activation predicts treatment improvement in patients with major depressive disorder", Journal of Psychiatric Research, vol. 45, No. 9, Sep. 2011, pp. 1214-1222.
Shen et al., "Synaptic Plasticity in Rat Subthalamic Nucleus Induced by High-Frequency Stimulation", Synapse, vol. 50, No. 4, Dec. 15, 2003, pp. 314-319.
Shimojo et al., "What visual perception tells us about mind and brain", Proceedings of the National Academy of Sciences, vol. 98, No. 22, Oct. 23, 2001, pp. 12340-12341.
Sibille et al., "GABA-related transcripts in the dorsolateral prefrontal cortex in mood disorders", International Journal of Neuropsychopharmacology, vol. 14, No. 6, Jul. 2011, pp. 721-734.
Siebner et al., "How does transcranial magnetic stimulation modify neuronal activity in the brain? Implications for studies of cognition", Cortex, vol. 45, No. 9, Oct. 2009, pp. 1035-1042.
Siebner et al., "Lasting cortical activation after repetitive TMS of the motor cortex: A glucose metabolic study", Neurology, vol. 54, No. 4, Feb. 22, 2000, pp. 956-963.

Siebner et al., "Patients with focal arm dystonia have increased sensitivity to slow-frequency repetitive TMS of the dorsal premotor cortex", Brain, vol. 126, No. 12, Dec. 1, 2003, pp. 2710-2725.
Silvanto et al., "Striate cortex (V1) activity gates awareness of motion", Nature Neuroscience, vol. 8, No. 2, Feb. 2005, pp. 143-144.
Smith et al., "Dendritic spikes enhance stimulus selectivity in cortical neurons in vivo", Nature, vol. 503, Nov. 7, 2013, pp. 115-120.
Smolen et al., "The right time to learn: mechanisms and optimization of spaced learning", Nature Reviews Neuroscience, vol. 17, Feb. 2016, pp. 77-88.
Sonmez et al., "Accelerated TMS for Depression: A systematic review and meta-analysis", Psychiatry Res., Mar. 2019, vol. 273, pp. 770-781, doi:10.1016/j.psychres.2018.12.041.
Sparing et al., "Repetitive Transcranial Magnetic Stimulation Effects on Language Function Depend on the Stimulation Parameters", Journal of Clinical Neurophysiology, vol. 18, No. 4, Jul. 2001, pp. 326-330.
Spronk et al., "Long Term Effects of Left Frontal rTMS on EEG and ERPs in Patients with Depression", Clinical EEG and Neuroscience, vol. 39, No. 3, Jul. 2008, pp. 118-124.
Stefan et al., "Induction of plasticity in the human motor cortex by paired associative stimulation", Brain, vol. 123, No. 3, Mar. 1, 2000, pp. 572-584.
Stokes et al., "Simple Metric For Scaling Motor Threshold Based on Scalp-Cortex Distance: Application to Studies Using Transcranial Magnetic Stimulation", J Neurophysiol, 94, 2005, pp. 4520-4527.
Suppa et al., "Theta burst stimulation induces after-effects on contralateral primary motor cortex excitability in humans", The Journal of Physiology, vol. 586, No. 18, Sep. 2008, pp. 4489-4500.
Takita et al., "Induction of stable long-termdepression in vivo in the hippocampal prefrontal cortex pathway", European Journal of Neuroscience, vol. 11, No. 11, Nov. 1999, pp. 4145-4148.
Tamas et al., "Identified Sources and Targets of Slow Inhibition in the Neocortex", Science, vol. 299, No. 5614, Mar. 21, 2003, pp. 1902-1905.
Terao et al., "Basic mechanisms of TMS", Journal of Clinical Neurophysiology, vol. 19, No. 4, Aug. 2002, pp. 322-343.
Trepel et al., "Long-term Potentiation in the Neocortex of the Adult, Freely Moving Rat", Cerebral Cortex, vol. 8, No. 8, Dec. 1998, pp. 719-729.
Vickery et al., "Metabotropic Glutamate Receptors Are Involved in Long-Term Potentiation in Isolated Slices of Rat Medial Frontal Cortex", Journal of Neurophysiology, vol. 78, No. 6, Dec. 1997, pp. 3039-3046.
Vink et al., "A novel concurrent TMS-fMRI method to reveal propagation patterns of prefrontal magnetic brain stimulation", Human Brain Mapping, vol. 39, No. 11, Nov. 2018, pp. 4580-4592.
Wagner et al., "Transcranial magnetic stimulation and stroke: A computer-based human model study", NeuroImage, vol. 30, No. 3, Apr. 15, 2006, pp. 857-870.
Wassermann, "Risk and safety of repetitive transcranial magnetic stimulation: report and suggested guidelines from the International Workshop on the Safety of Repetitive Transcranial Magnetic Stimulation", Electroencephalography and Clinical Neurophysiology, vol. 108, 1998, pp. 1-16.
Weigand et al., "Prospective Validation That Subgenual Connectivity Predicts Antidepressant Efficacy of Transcranial Magnetic Stimulation Sites", Biological Psychiatry, vol. 84, No. 1, Jul. 1, 2018, pp. 28-37.
Williams, "Accelerated rTMS: Pragmatic Considerations for the Development of an Inpatient rTMS Approach", Brain Stimulation, Mar. 2017, vol. 10, Issue No. 2, DOI: 10.1016/J.BRS.2017.01.269, p. 427.
Williams et al., "Five-Year Follow-Up of Bilateral Epidural Prefrontal Cortical Stimulation for Treatment-Resistant Depression", Brain Stimul, 9, 23016, pp. 897-904.
Williams et al., "High-dose spaced theta-burst TMS as a rapid-acting antidepressant in highly refractory despression", Brain, vol. 141, No. 3, Mar. 2018.

(56) References Cited

OTHER PUBLICATIONS

Williams et al., "Optimization of epidural cortical stimulation for treatment-resistant depression", Brain Stimulation, vol. 11, No. 1, Jan.-Feb. 2018, pp. 239-240.
Wozny et al., "Specificity of Synaptic Connectivity between Layer 1 Inhibitory Interneurons and Layer 2/3 Pyramidal Neurons in the Rat Neocortex", Cerebral Cortex, vol. 21, No. 8, Aug. 1, 2011, pp. 1818-1826.
Wu et al., "Theta-Burst Repetitive Transcranial Magnetic Stimulation For Treatment-Resistant Obsessive-Compulsive Disorder With Concomitant Depression", The Journal of Clinical Psychiatry, vol. 71, No. 4, Apr. 2010, pp. 504-506.
Xu et al., "Nonlinear dendritic integration of sensory and motor input during an active sensing task", Nature, vol. 492, Dec. 13, 2012, pp. 247-251.
Yip et al., "61% of unmedicated treatment resistant depression patients who did no respond to acute TMS treatment responded after four weeks of twice weekly deep TMS in the Brainsway pivotal trial", Brain stimul, 10, 2017, pp. 847-849.
Zanto et al., "Causal role of the prefrontal cortex in top-down modulation of visual processing and working memory", Nature Neuroscience, vol. 14, No. 5, May 2011, pp. 656-661.
Ziemann, "TMS in cognitive neuroscience: Virtual lesion and beyond", Cortex, vol. 46, No. 1, Jan. 2010, pp. 124-127.
Ziemann et al., "Modulation of Plasticity in Human Motor Cortex after Forearm Ischemic Nerve Block", The Journal of Neuroscience, vol. 18, No. 3, Feb. 1, 1998, pp. 1115-1123.
A New Study to Treat Depression, https://www.youtube.com/watch?v=2oZ2eHecvY4, Oct. 27, 2017, 1 page.
Extended European Search Report for European Application No. 19738551.1, Search completed Aug. 16, 2021, dated Aug. 25, 2021, 13 Pgs.
International Preliminary Report on Patentability for International Application No. PCT/US2019/013353, Report issued Jul. 14, 2020, dated Jul. 23, 2020, 7 Pgs.
International Search Report and Written Opinion for International Application No. PCT/US2019/013353, Search completed Jul. 31, 2019, dated Nov. 14, 2019, 13 Pgs.
International Search Report and Written Opinion for International Application No. PCT/US2021/054633, Search completed Dec. 9, 2021, dated Jan. 12, 2022, 14 Pgs.
Aguirre et al., "Age predicts low-frequency transcranial magnetic stimulation efficacy in major depression", Journal of Affective Disorders, vol. 130, No. 3, May 2011, Electronic Publication: Nov. 18, 2010, pp. 466-469.
Allen et al., "The stability of resting frontal electroencephalographic asymmetry in depression", Psychophysiology, vol. 41, No. 2, Mar. 2004, pp. 269-280.
Anderson et al., "Repetitive transcranial magnetic stimulation for treatment resistant depression: Re-establishing connections", Clinical Neurophysiology, vol. 127, No. 11, Nov. 2016, pp. 3394-3405.
Baeken et al., "Accelerated HF-rTMS in treatment-resistant unipolar depression: Insights from subgenual anterior cingulate functional connectivity", The World Journal of Biological Psychiatry, vol. 15, No. 4, Jan. 21, 2014, pp. 286-297.
Baeken et al., "Intensive HF-rTMS treatment in refractory medication- resistant unipolar depressed patients", Journal of Affective Disorders, Available online Jul. 26, 2013, vol. 151, No. 2, pp. 625-631.
Baeken et al., "Neurobiological mechanisms of repetitive transcranial magnetic stimulation on the underlying neurocircuitry in unipolar depression", Dialogues in Clinical Neuroscience, vol. 13, No. 1, Mar. 2011, pp. 139-145.
Baeken et al., "The Impact of Accelerated HF-rTMS on the Subgenual Anterior Cingulate Cortex in Refractory Unipolar Major Depression: Insights From 18FDG PET Brain Imaging", Brain Stimulation, vol. 8, No. 4, Jul.-Aug. 2015, pp. 808-815.
Bakker et al., "rTMS of the dorsomedial prefrontal cortex for major depression: safety, tolerability, effectiveness, and outcome predictors for 10 Hz versus intermittent theta-burst stimulation", Brain Stimul, vol. 8, No. 2, 2015, pp. 208-215.
Berenyi et al., "Closed-Loop Control of Epilepsy by Transcranial Electrical Stimulation", Science, vol. 337, Aug. 10, 2012, pp. 735-737.
Berlim et al., "A systematic review and meta-analysis on the efficacy and acceptability of bilateral repetitive transcranial magnetic stimulation (rTMS) for treating major depression", Psychological Medicine, vol. 43, No. 11, Nov. 2013, Electronic Publication: Dec. 3, 2012, pp. 2245-2254.
Berlim et al., "Blinding integrity in randomized sham-controlled trials of repetitive transcranial magnetic stimulation for major depression: a systematic review and meta-analysis", International Journal of Neuropsychopharmacology, vol. 16, No. 5, Jun. 2013, Electronic Publication: Feb. 11, 2013, pp. 1173-1181.
Berlim et al., "Clinically Meaningful Efficacy and Acceptability of Low- Frequency Repetitive Transcranial Magnetic Stimulation (rTMS) for Treating Primary Major Depression: A Meta-Analysis of Randomized, Double-Blind and Sham-Controlled Trials", Neuropsychopharmacology, vol. 38, No. 4, Mar. 2013, Electronic Publication: Nov. 19, 2012, pp. 543-551.
Berlim et al., "High-Frequency Repetitive Transcranial Magnetic Stimulation Accelerates and Enhances the Clinical Response to Antidepressants in Major Depression: A Meta-Analysis of Randomized, Double-Blind, and Sham-Controlled Trials", Journal of Clinical Psychiatry, vol. 74, No. 2, Feb. 2013, pp. e122-e129.
Berlim et al., "Response, remission and drop-out rates following high- frequency repetitive transcranial magnetic stimulation (rTMS) for treating major depression: a systematic review and meta-analysis of randomized, double-blind and sham-controlled trials", Psychological Medicine, vol. 44, No. 2, Jan. 2014, Electronic Publication: Mar. 18, 2013, pp. 225-239.
Blumberger et al., "Effectiveness of theta burst versus high-frequency repetitive transcranial magnetic stimulation in patients with depression (THREE-D): a randomised non-inferiority trial", The Lancet, vol. 391, No. 10131, Apr. 28, 2018, pp. 1683-1692.
Brakemeier et al., "Patterns of response to repetitive transcranial magnetic stimulation (rTMS) in major depression: Replication study in drug-free patients", Journal of Affective Disorders, vol. 108, No. 1-2, May 2008, pp. 59-70.
Camprodon et al., "Two Phases of V1 Activity for Visual Recognition of Natural Images", Journal of Cognitive Neuroscience, vol. 22, No. 6, Jun. 2010, pp. 1262-1269.
Cao et al., "Augmenting saturated LTP by broadly spaced episodes of theta-burst stimulation in hippocampal area CA1 of adult rats and mice", Journal of Neurophysiology, vol. 112, No. 8, Oct. 15, 2014, pp. 1916-1924.
Capocchi et al., "Theta burst stimulation is optimal for induction of LTP at both apical and basal dendritic synapses on hippocampal CA1 neurons", Brain Research, vol. 591, No. 2, Sep. 25, 1992, pp. 332-336.
Cárdenas-Morales et al., "Exploring the after-effects of theta burst magnetic stimulation on the human motor cortex: A functional imaging study", Human Brain Mapping, vol. 32, No. 11, Nov. 2011, Electronic Publication: Dec. 22, 2010, pp. 1948-1960.
Cash et al., "Subgenual Functional Connectivity Predicts Antidepressant Treatment Response to Transcranial Magnetic Stimulation: Independent Validation and Evaluation of Personalization", Biological Psychiatry, Articles in Press, Jan. 19, 2019, 5 pgs.
Cazzoli et al., "Theta burst stimulation reduces disability during the activities of daily living in spatial neglect", Brain, 135, Part 11, 2012, pp. 3426-3439.
Chalifoux et al., "GABAB Receptor Modulation of Voltage-Sensitive Calcium Channels in Spines and Dendrites", Journal of Neuroscience, vol. 31, No. 11, Mar. 16, 2011, pp. 4221-4232.
Chen et al., "Depression of motor cortex excitability by low-frequency transcranial magnetic stimulation", Neurology, vol. 48, No. 5, May 1997, pp. 1398-1403.
Chen et al., "Mechanisms of Cortical Reorganization in Lower-Limb Amputees", The Journal of Neuroscience, vol. 18, No. 9, May 1, 1998, pp. 3443-3450.
Cheng et al., "Different forms of prefrontal theta burst stimulation for executive function of medication-resistant depression: Evidence

(56) References Cited

OTHER PUBLICATIONS from a randomized sham-controlled study", Prog Neuropsychopharmacol Biol Psychiatry, vol. 66, 2016, pp. 35-40.

Chistyakov et al., "Safety, tolerability and preliminary evidence for antidepressant efficacy of theta-burst transcranial magnetic stimulation in patients with major depression.", International Journal of Neuropsychopharmacology, vol. 13, No. 3, Apr. 2010, Electronic Publication: Feb. 4, 2010, pp. 387-393.

Cho et al., "Continuous theta burst stimulation of right dorsolateral prefrontal cortex induces changes in impulsivity level", CIHR Author Manuscript, 16 pgs, Published in final form as: Brain Stimulation, vol. 3, No. 3, Jul. 2010, pp. 170-176.

Chung et al., "Impact of different intensities of intermittent theta burst stimulation on the cortical properties during TMS-EEG and working memory performance", Human Brain Mapping, vol. 39, No. 2, Feb. 2018, pp. 783-802.

Chung et al., "The effect of single and repeated prefrontal intermittent theta burst stimulation on cortical reactivity and working memory", Brain Stimulation, vol. 11, No. 3, May-Jun. 2018, pp. 566-574.

Chung et al., "The effects of individualised intermittent theta burst stimulation in the prefrontal cortex: A TMS-EEG study", Human Brain Mapping, vol. 40, No. 2, Feb. 1, 2019, pp. 608-627.

Cichon et al., "Branch-specific dendritic Ca2+ spikes cause persistent synaptic plasticity", Nature, vol. 520, No. 7546, Apr. 9, 2015, Electronic Publication: Mar. 30, 2015, pp. 180-185.

Ciobanu et al., "rTMS for pharmacoresistant major depression in the clinical setting of a psychiatric hospital: effectiveness and effects of age", Journal of Affective Disorders, vol. 150, No. 2, Sep. 5, 2013, pp. 677-681.

Cohen et al., "Effects of coil design on delivery of focal magnetic stimulation. Technical considerations", Electroencephalography and Clinical Neurophysiology, vol. 75, No. 4, Apr. 1990, pp. 350-357.

Cole et al., "Stanford Accelerated Intelligent Neuromodulation Therapy for Treatment-Resistant Depression", American Journal of Psychiatry, Aug. 1, 2020, vol. 177, Issue 8, 14 pgs.

Daskalakis et al., "Repetitive transcranial magnetic stimulation for major depressive disorder: a review.", The Canadian Journal of Psychiatry, vol. 53, No. 9, Sep. 2008, pp. 555-566.

Defelipe, "The evolution of the brain, the human nature of cortical circuits, and intellectual creativity", Frontiers in Neuroanatomy, vol. 5, No. 29, May 16, 2011, 17 pgs.

Desmyter et al., "Accelerated Intermittent Theta Burst Stimulation for Suicide Risk in Therapy-Resistant Depressed Patients: A Randomized, Sham-Controlled Trial", Frontiers in Human Neuroscience, vol. 10, No. 480, Sep. 27, 2016, 7 pgs.

Desmyter et al., "The Acute Effects of Accelerated Repetitive Transcranial Magnetic Stimulation on Suicide Risk in Unipolar Depression: Preliminary Results", Psychiatria Danubina, vol. 26, Suppl. 1, Nov. 2014, pp. 48-52.

Diekhoff-Krebs et al., "Interindividual differences in motor network connectivity and behavioral response to iTBS in stroke patients", NeuroImage: Clinical, vol. 15, 2017, pp. 559-571.

Downar, "Optimizing the Inter-Session Interval for Accelerated rTMS", Brain Stimulation, Mar. 2017, vol. 10, Issue No. 2, pp. 456-457, DOI: 10.1016/J.BRS.2017.01.340.

Drysdale et al., "Resting-state connectivity biomarkers define neurophysiological subtypes of depression", Nat. Med., Author Manuscript, Oct., 2, 2017, 35 pgs.

Drysdale et al., "Resting-state connectivity biomarkers define neurophysiological subtypes of depression", Nature Medicine, No. 23, 2017, pp. 28-38, Published online Dec. 5, 2016, printed Mar. 21, 2017 from http://www.nature.com/nm/journal/v23/n1/ full/nm.4246. html, 5 pgs.

Friston, Karl J., "Functional and Effective Connectivity in Neuroimaging: a Synthesis", Human Brain Mapping, vol. 2, Issue No. 1-2, 1994, pp. 56-78.

International Preliminary Report on Patentability for International Application PCT/US2021/054633, Report issued Apr. 13, 2023, dated Apr. 27, 2023, 06 Pgs.

\* cited by examiner

SYSTEMS AND METHODS FOR TARGETED NEUROMODULATION

CROSS-REFERENCE TO RELATED APPLICATIONS

The current application claims the benefit of and priority under 35 U.S.C. § 119(e) to U.S. Provisional Patent Application Ser. No. 63/090,680 entitled "Systems and Methods for Neuronavigation" filed Oct. 12, 2020, the disclosure of which is hereby incorporated by reference in its entirety for all purposes.

FIELD OF THE INVENTION

The present invention generally relates to neuromodulation therapy, and (more specifically) to generating personalized stimulation targets.

BACKGROUND

Brain stimulation therapies can be delivered in a number of ways such as (but not limited to) transcranial magnetic stimulation (TMS) and deep brain stimulation (DBS). TMS. Brain stimulation therapies are often delivered at or towards a particular region of a patient's brain in order to treat a condition of the patient.

Radiological imaging enables non-invasive scanning of internal organs. Common brain imaging techniques involve the use of magnetic resonance imaging (MRI) machines, and a variant of MRI referred to as functional MRI (fMRI) which is capable of measuring brain activity by measuring changes associated with blood flow. MRI, as opposed to fMRI, is often referred to as "structural" as it examines only the anatomy of the brain, and not brain activity.

SUMMARY OF THE INVENTION

Systems and methods for targeted neuromodulation in accordance with embodiments of the invention are illustrated. One embodiment includes a targeted neuronavigation system including a processor and a memory containing a targeting application, where the targeting application directs the processor to obtain patient brain data, where the patient brain data comprises a structural magnetic resonance imaging (sMRI) scan and at least one functional magnetic resonance imaging (fMRI) scan of a patient's brain, map a reference region of interest (ROI) and at least one search ROI to the patient's brain using the sMRI scan and at least one fMRI scan, where the reference ROI describes a region to be indirectly impacted via a brain stimulation therapy, and where the at least one search ROI describes at least one region to be directly targeted by the brain stimulation therapy, derive an individualized map of ROI parcellation, where the individualized map of ROI parcellation describes the reference ROI as a plurality of reference parcels, and describes the at least one search ROI as a plurality of candidate parcels, extract relationships between the plurality of candidate parcels and the plurality of reference parcels, calculate a target score for candidate parcels in the plurality of candidate parcels based on the extracted relationships, select a target parcel from the plurality of candidate parcels based on the target score, and provide the target parcel.

In another embodiment, the targeting application further directs the process to provide the brain stimulation therapy to the target parcel in order to treat a mental condition of the patient.

In a further embodiment, the mental condition is major depressive disorder.

In still another embodiment, the mental condition is suicidal ideation.

In a still further embodiment, the brain stimulation therapy is selected from the group consisting of: transcranial magnetic stimulation; transcranial direct current stimulation; and electrical stimulation delivered via an implantable electrostimulator.

In yet another embodiment, the targeting application further directs the processor to discard fMRI scans that deviate from expected whole brain network connectivity.

In a yet further embodiment, to derive the individualized map of ROI parcellation, the targeting application further directs the processor to randomly subsample voxels in the reference and at least one search ROIs, cluster the subsample of voxels, record a clustering assignment, and label clusters in the clustering assignment as candidate parcels or reference parcels based on their location.

In another additional embodiment, to derive the individualized map of ROI parcellation, the targeting application further directs the processor to randomly subsample voxels in the reference and at least one search ROIs as a first subsample of voxels, cluster the first subsample of voxels, record a first clustering assignment, randomly subsample voxels in the reference and at least one search ROIs as a second subsample of voxels, cluster the second subsample of voxels, record a second clustering assignment, merge the first clustering assignment and second clustering assignment using consensus clustering, and label clusters in the merged clustering assignment as candidate parcels or reference parcels based on their location.

In a further additional embodiment, to derive the individualized map of ROI parcellation, the targeting application further directs the processor to split spatially disjoint clusters.

In another embodiment again, the target score is calculated based on at least one factor from the group consisting of: parcel size, parcel depth, parcel shape, parcel homogeneity, functional connectivity strength to the reference ROI, and a network connectivity score.

In a further embodiment again, the network connectivity score reflects anticorrelation between a default mode network and a dorsal attention network of the patient's brain.

In still yet another embodiment, a method of targeted neuronavigation includes obtaining patient brain data, where the patient brain data includes a structural magnetic resonance imaging (sMRI) scan and at least one functional magnetic resonance imaging (fMRI) scan of a patient's brain, mapping a reference region of interest (ROI) and at least one search ROI to the patient's brain using the sMRI scan and at least one fMRI scan, where the reference ROI describes a region to be indirectly impacted via a brain stimulation therapy, and where the at least one search ROI describes at least one region to be directly targeted by the brain stimulation therapy, deriving an individualized map of ROI parcellation, where the individualized map of ROI parcellation describes the reference ROI as a plurality of reference parcels, and describes the at least one search ROI as a plurality of candidate parcels, extracting relationships between the plurality of candidate parcels and the plurality of reference parcels, calculating a target score for candidate parcels in the plurality of candidate parcels based on the extracted relationships, selecting a target parcel from the plurality of candidate parcels based on the target score, and providing the target parcel. In many embodiments, obtaining patient brain data may be accomplished by accessing patient brain data that has previously been uploaded to or transmitted to the target identification system; requesting patient brain data from a remote institution, computer system, or database; or by accessing hardware such as MRI or other imaging hardware to cause acquisition of patient brain data.

In a still yet further embodiment, the method further includes providing the brain stimulation therapy to the target parcel in order to treat a mental condition of the patient.

In still another additional embodiment, the mental condition is major depressive disorder.

In a still further additional embodiment, the mental condition is suicidal ideation.

In still another embodiment again, the brain stimulation therapy is selected from the group consisting of: transcranial magnetic stimulation; transcranial direct current stimulation; and electrical stimulation delivered via an implantable electrostimulator.

In a still further embodiment again, the method further includes discarding fMRI scans that deviate from expected whole brain network connectivity.

In yet another additional embodiment, wherein deriving the individualized map of ROI parcellation includes randomly subsampling voxels in the reference and at least one search ROIs, clustering the subsample of voxels, and recording a clustering assignment, labeling clusters in the clustering assignment as candidate parcels or reference parcels based on their location.

In a yet further additional embodiment, wherein deriving the individualized map of ROI parcellation includes randomly subsampling voxels in the reference and at least one search ROIs as a first subsample of voxels, clustering the first subsample of voxels; recording a first clustering assignment, randomly subsampling voxels in the reference and at least one search ROIs as a second subsample of voxels, clustering the second subsample of voxels, and recording a second clustering assignment, merging the first clustering assignment and second clustering assignment using consensus clustering, and labeling clusters in the merged clustering assignment as candidate parcels or reference parcels based on their location.

In yet another embodiment again, deriving the individualized map of ROI parcellation further includes splitting spatially disjoint clusters.

In a yet further embodiment again, the target score is calculated based on at least one factor from the group consisting of: parcel size, parcel depth, parcel shape, parcel homogeneity, functional connectivity strength to the reference ROI, and a network connectivity score.

In another additional embodiment again, the network connectivity score reflects anticorrelation between a default mode network and a dorsal attention network of the patient's brain.

In a further additional embodiment again, a system for treating major depressive disorder includes a transcranial magnetic stimulation device, a neuronavigation device, a processor, and a memory containing a targeting application, where the targeting application directs the processor to obtain patient brain data, where the patient brain data comprises a structural magnetic resonance imaging (sMRI) scan and at least one functional magnetic resonance imaging (fMRI) scan of a patient's brain, map a reference region of interest (ROI) and at least one search ROI to the patient's brain using the sMRI scan and at least one fMRI scan, where the reference ROI describes a region to be indirectly impacted via the transcranial magnetic stimulation device, and where the at least one search ROI describes at least one region to be directly targeted by the brain stimulation therapy, derive an individualized map of ROI parcellation, where the individualized map of ROI parcellation describes the reference ROI as a plurality of reference parcels, and describes the at least one search ROI as a plurality of candidate parcels, extract relationships between the plurality of candidate parcels and the plurality of reference parcels, calculate a target score for candidate parcels in the plurality of candidate parcels based on the extracted relationships, select a target parcel from the plurality of candidate parcels based on the target score, and apply transcranial magnetic stimulation to the target parcel using the transcranial magnetic stimulation device and/or neuronavigation device in order to treat major depressive disorder.

In yet another additional embodiment again, the target parcel is transmitted from a cloud computing platform to a neuronavigation system.

In still yet another additional embodiment, a method of treating major depressive disorder includes obtaining patient brain data, where the patient brain data comprises a structural magnetic resonance imaging (sMRI) scan and at least one functional magnetic resonance imaging (fMRI) scan of a patient's brain, mapping a reference region of interest (ROI) and at least one search ROI to the patient's brain using the sMRI scan and at least one fMRI scan, where the reference ROI describes a region to be indirectly impacted via a brain stimulation therapy, and where the at least one search ROI describes at least one region to be directly targeted by the brain stimulation therapy, deriving an individualized map of ROI parcellation, where the individualized map of ROI parcellation describes the reference ROI as a plurality of reference parcels, and describes the at least one search ROI as a plurality of candidate parcels, extracting relationships between the plurality of candidate parcels and the plurality of reference parcels, calculating a target score for candidate parcels in the plurality of candidate parcels based on the extracted relationships, selecting a target parcel from the plurality of candidate parcels based on the target score, and treating major depressive disorder by applying transcranial magnetic stimulation to the target parcel using a transcranial magnetic stimulation device and/or a neuronavigation device.

In still yet again another additional embodiment, the transcranial magnetic stimulation is accelerated theta burst stimulation.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
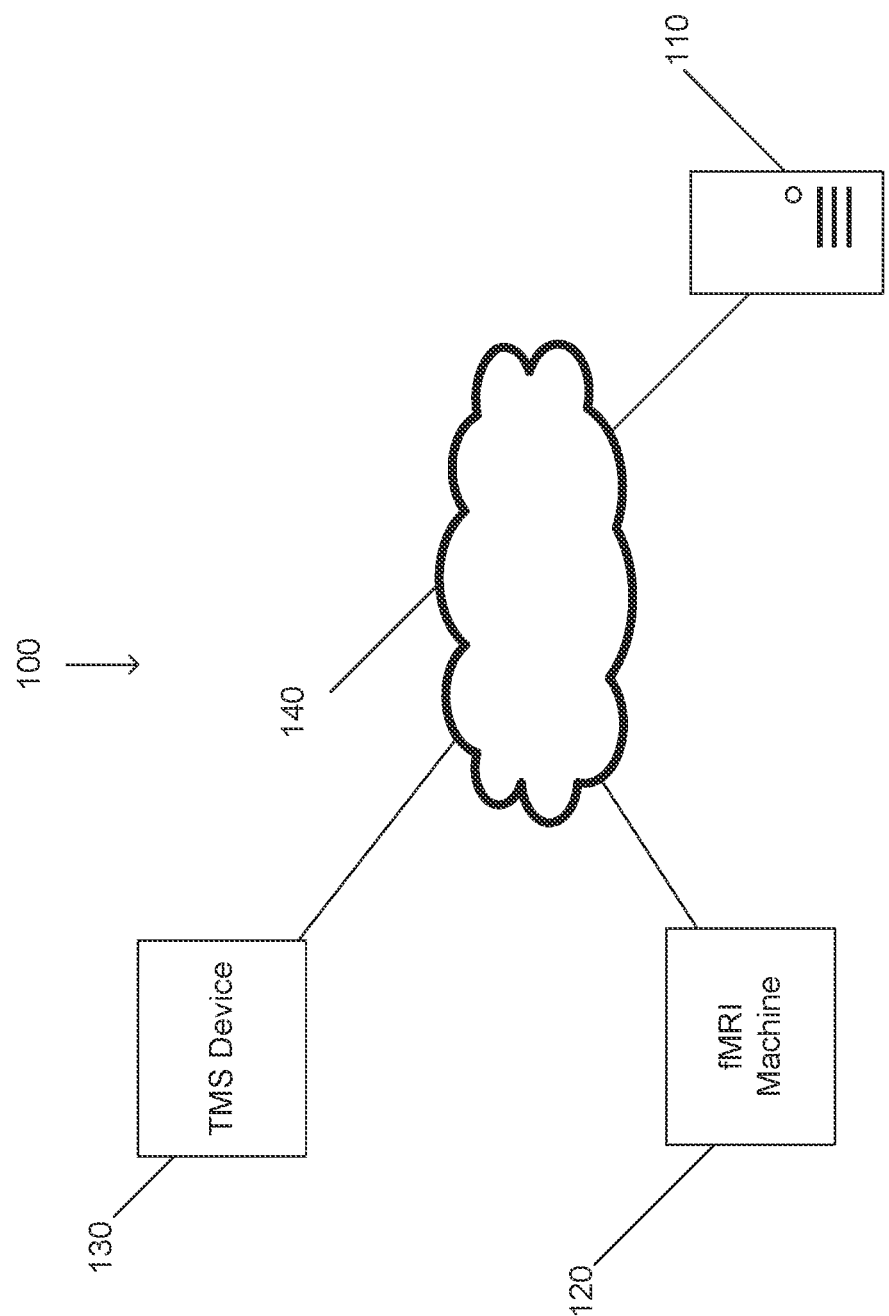
FIG. 1 illustrates a targeted neuromodulation system in accordance with an embodiment of the invention.

Mental health conditions and other neurological problems are a significant field of medicine with profound importance for both patients and society as a whole. For example, depression and suicidal ideation represent chronic public health issues. However, treatment for these conditions have conventionally been addressed with pharmaceuticals, and in some treatment resistant cases, using surgery and/or electroconvulsive therapy (ECT). These methods can have significant side effects that are both mental and physical. In contrast, a form of therapy called transcranial magnetic stimulation (TMS) has arisen as a viable non-invasive treatment option with minimal side effects reported.

TMS involves applying a magnetic field to a particular region of the brain in order to depolarize or hyperpolarize neurons at the target region. Generally, the target region is selected by a medical professional based on its relationship with the patient's condition. For example, the dorsolateral prefrontal cortex (DLPFC) is known to be involved with major depressive disorder. However, the exact location of the DLPFC in an individual can be difficult to manually identify. Even when it can be identified, there may in fact be a particular subregion of the DLPFC which would be the most effective target for the individual patient based on their idiosyncratic brain. Further, there may even be other regions in the brain that would provide better stimulation targets for the patient. As every brain is at least slightly different, a personalized way of generating stimulation targets for an individual can provide better treatment outcomes.

An additional limitation of many TMS devices is the depth at which they can induce a current in a patient's brain. Often, TMS devices cannot target deep brain structures. However, there are numerous large-scale networks throughout the brain that have been identified. For example, the default mode network (DMN) is a network which appears to be involved with numerous tasks such as wakeful rest. By way of further example, the dorsal attention network (DAN) is thought to be key in voluntary orienting of visuospatial attention, and similarly the ventral attention network (VAN) reorients attention towards salient stimuli. Connectivity between different regions of the brain can provide an opportunity in TMS and other brain stimulation therapies whereby a more surface brain structure which is strongly connected to a deeper brain structure can be stimulated to effect change in the deeper brain region. Further, stimulation of connected networks can have significant impacts on structures within or otherwise connected to the network. Some networks in particular such as (but not limited to) the DMN, the DAN, and the VAN have particular experimentally determined relationships to major depressive disorder and suicidal ideation. Networks with relationships to a particular mental condition to be treated can be given additional priority.

Given the complex nature of the brain, when applying a neuromodulation therapy (like TMS), the location at which the stimulation is delivered can have a significant impact on the outcome of the treatment. Targeting as discussed herein refers to the process of identifying target structures within a patient's brain for stimulation in order to treat mental health conditions. While current targeting methods can yield workable targets, many conventional methods have significant failings. For example, targeting often takes place using one scan from a patient and cannot incorporate multiple scans over time. Due to scanning noise and limited test-retest reliability of fMRI, deriving a target based on a single scan is more likely to be affected by noise and lead to a compromised levels of target reliability. Reliability limitation may be even more prominent for methods that employ voxel clustering for target detection, especially if clustering procedure is highly sensitive to noise and signal loss. Further, clustering procedures used for this purpose do not always consider the spatial relations between the voxels, which may lead to impractical results. Turning now to the drawings, systems and methods described herein seek to address these limitations, and provide a more robust targeting framework that produces more effective individualized stimulation targets for more effective treatment. In many embodiments, the targets produced using systems and methods described herein are subsequently used as the target in a neuromodulation therapy such as (but not limited to), TMS, transcranial direct current stimulation (tDCS), as the implantation location for one or more stimulation electrodes, and/or as the target for any number of different neuromodulation modalities as appropriate to the requirements of specific applications of embodiments of the invention. Targeting systems in accordance with embodiments of the invention are discussed below.

Targeted Neuromodulation Systems

Targeted neuromodulation systems are capable of obtaining and/or accessing scans of a patient's brain, and identifying one or more individualized targets for brain stimulation therapy. In many embodiments, targeting systems may be integrated into other medical devices, such as (but not limited to) TMS devices or neuronavigation devices. In various embodiments, targeting systems not only can generate individualized targets, but also include or be integrated with neuronavigation devices to identify where a TMS coil should be placed to correctly stimulate the target. In many embodiments, targeted neuromodulation systems can further apply neuromodulation to the generated target via a neuromodulation device such as (but not limited to) a TMS device, a tDCS device, an implantable neurostimulator, and/or any other neurostimulation device as appropriate to the requirements of specific applications of embodiments of the invention.

Turning now to FIG. 1, a targeted neuromodulation system in accordance with an embodiment of the invention is illustrated. Targeted neuromodulation system 100 includes a target generator 110. Targeting generators can be implemented using any number of different computing platforms such as (but not limited to) desktop computers, laptops, server computers and/or clusters, smartphones, tablet PCs, and/or any other computing platform capable of executing logic instructions as appropriate to the requirements of specific applications of embodiments of the invention. In many embodiments, target generators determine personalized and/or partially-personalized targets within an individual's brain.

Targeted neuromodulation system 100 further includes an fMRI machine 120 and a TMS device 130. In many embodiments, the fMRI machine is capable of obtaining both structural and functional MRI images of a patient. The TMS device 130 can deliver brain stimulation therapy to the target selected by the target generator 110. However, as can readily be appreciated, alternative imaging modalities (e.g. computed tomography, positron emission tomography, electroencephalography, etc.), and alternative brain stimulation devices can be used (e.g. implantable stimulators) as appropriate to the requirements of specific applications of embodiments of the invention; alternatively, the targeting system 100 may not include its own imaging equipment, and may receive imaging or other brain data from one or more imaging systems that are distinct from the neuromodulation system 100.

In many embodiments, the targeted neuromodulation system 100 includes a neuronavigation device which guides delivery of brain stimulation therapy by TMS device 130 to a target selected by the target generator 110. This neuronavigation device may be integrated into the targeting generator 110 or separate (not shown) from the targeting system 110. In numerous embodiments, neuronavigation devices assist in delivering brain stimulation therapy to one or more targets generated by a targeting system; for instance, by determining the rotational and translational position of a stimulating coil and head and displaying an image to guide a user to position the stimulating coil correctly, or by additionally using a mechanical actuator such as a robotic arm to position the stimulating coil correctly. As can be readily appreciated the specific function of a neuronavigation device can be varied depending on the type of neuromodulation being applied.

In many embodiments, the fMRI, TMS device, targeting system, and/or neuronavigation device are connected via a network 140. The network can be a wired network, a wireless network, or any combination thereof. Indeed, any number of different networks can be combined to connect the components. However, it is not a requirement that all components of the system be in communication via a network. Target generators are capable of performing without operative connections between other components. Indeed, as can be readily appreciated, while a specific targeted neuromodulation system is illustrated in FIG. 1, any number of different system architectures can be used without departing from the scope or spirit of the invention. For example, in many embodiments, targeted neuromodulation systems can include different neuromodulation devices that provide different stimulation modalities.

Figure 2:
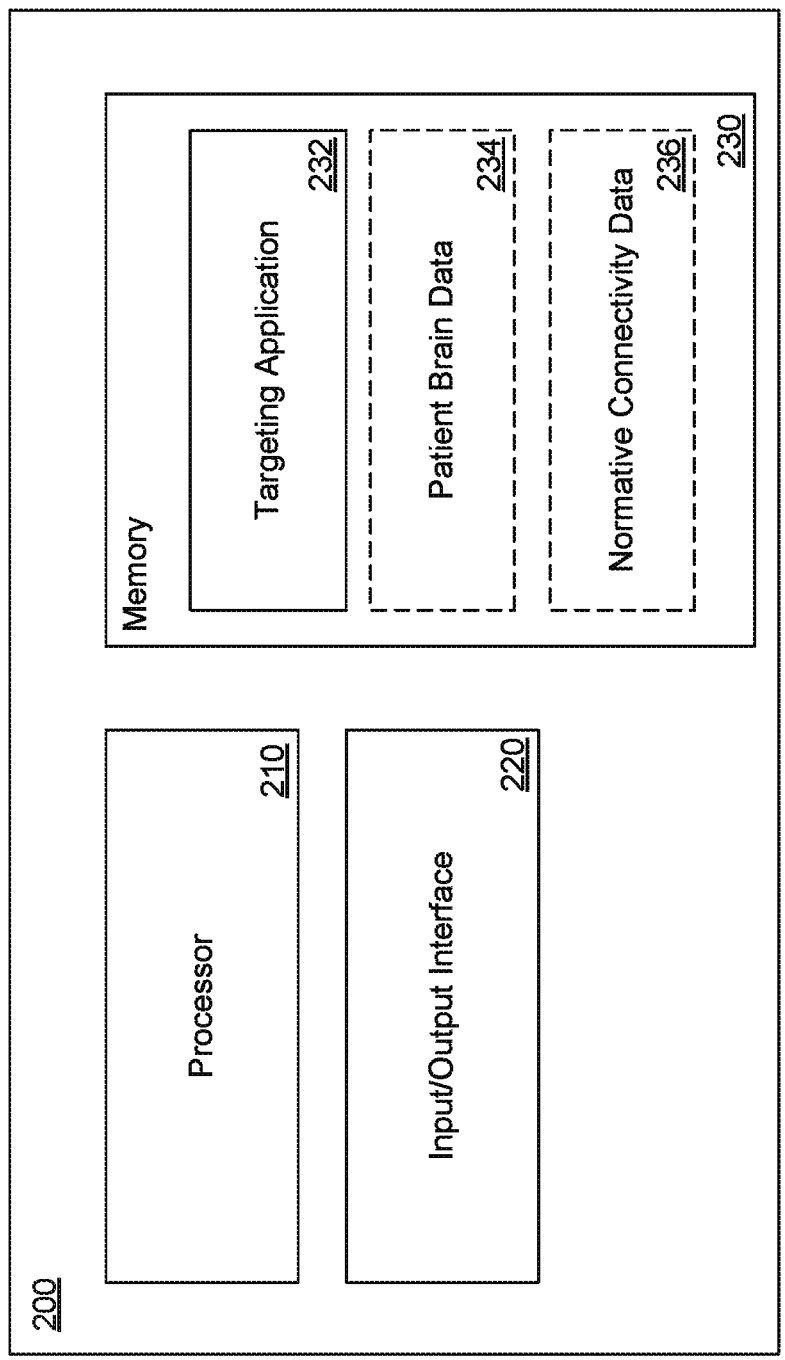
FIG. 2 illustrates a target generator in accordance with an embodiment of the invention.

When targeting systems are provided with patient brain data, they are capable of generating individualized targets. Turning now to FIG. 2, a target generator architecture in accordance with an embodiment of the invention is illustrated. Target generator 200 includes a processor 210. However, in many embodiments, more than one processor can be used. In various embodiments, the processor can be made of any logic processing circuitry such as (but not limited to) central processing units (CPUs), graphics processing units (GPUs), application specific integrated circuits (ASICs), field programmable gate arrays (FPGAs), and/or any other circuit as appropriate to the requirements of specific applications of embodiments of the invention.

The target generator 200 further includes an input/output (I/O) interface 220. I/O interfaces are capable of transferring data between connected components such as (but not limited to) displays, TMS devices, fMRI machines, other treatment devices and/or imaging devices, and/or any other computer component as appropriate to the requirements of specific applications of embodiments of the invention. The target generator further includes a memory 230. The memory can be implemented using volatile memory, non-volatile memory, or any combination thereof. As can be readily appreciated, any machine-readable storage media can be used as appropriate to the requirements of specific applications of embodiments of the invention.

The memory 230 contains a targeting application 232. The targeting application is capable of directing the processor to execute various target generation processes. The memory 230 is also capable of storing patient brain data 234. Patient brain data describes brain scans of the patient such as, but not limited to, structural MRI and functional MRI scans. In numerous embodiments, the memory 230 can further contain normative connectivity data 236 describing expected generalized connectivity networks for a standard brain model.

While particular target generator architectures and target generators are discussed in accordance with embodiments of the invention above, any number of different architectures and hardware designs can be used without departing from the scope or spirit of the invention. For example, in many embodiments, different stimulation modalities can be used. In various embodiments, transcranial direct current stimulation is used. In numerous embodiments, implantable electrical neurostimulators are used to directly stimulate brain tissue. Target generation processes for generating individualized stimulation targets are discussed in further detail below.

Generating Individualized Stimulation Targets

Some brain stimulation methods will work with some degree of efficacy without individualized, precision targeting. However, providing stimulation to a particular region of the brain to attempt to maximize the impact of treatment for an individual is highly beneficial. Various existing methodologies that attempt to generate personalized targets fail to fully consider the existing network connectivity in the brain and/or naïvely cluster regions within the brain. Target identification processes described herein can provide higher accuracy stimulation targets for an individual based on their personal brain network connectivity.

Figure 3:
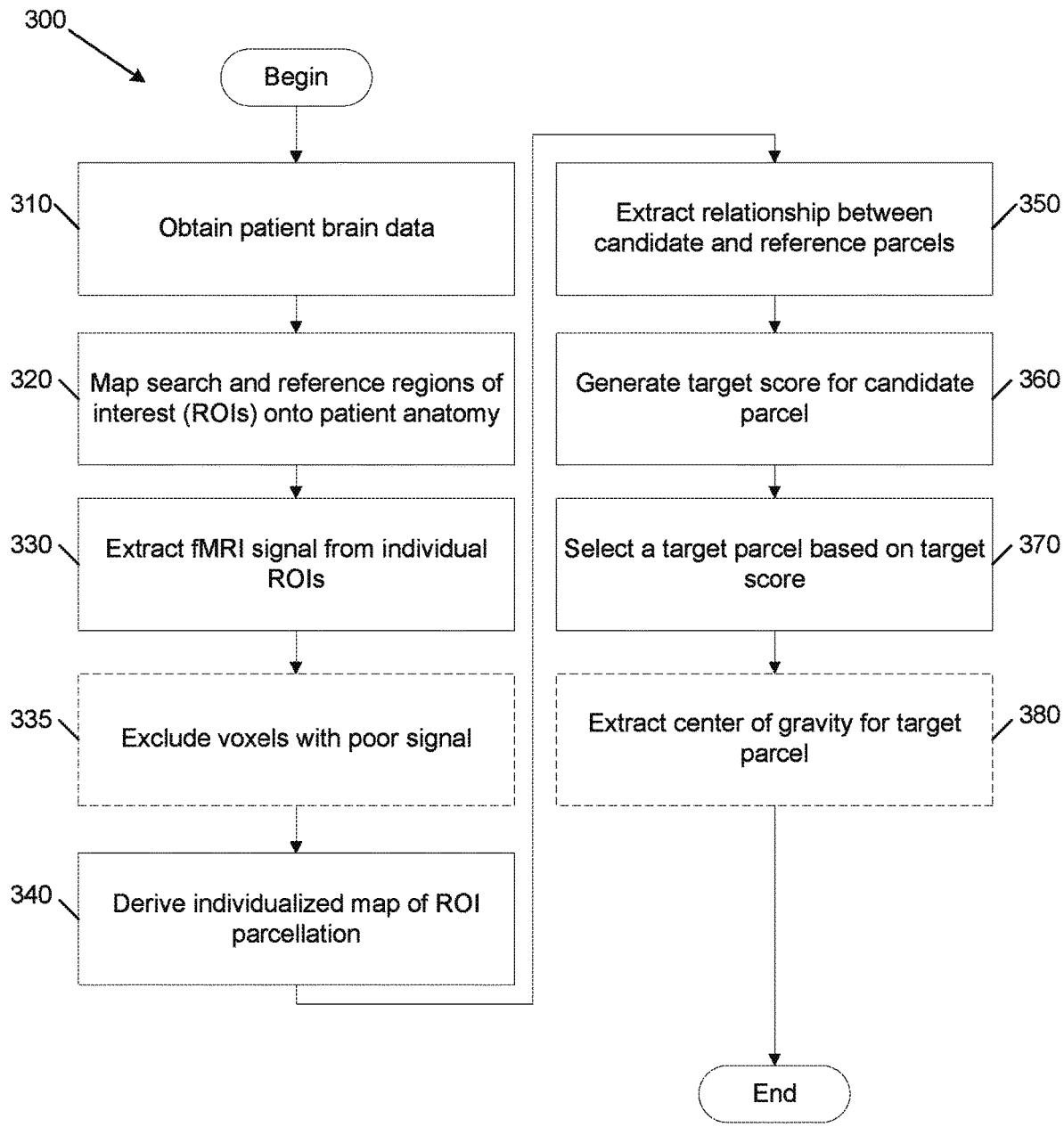
FIG. 3 is a flow chart illustrating a targeting process for generating an individualized target in accordance with an embodiment of the invention.

Turning now to FIG. 3, a flow chart of a target identification process for generating an individualized stimulation target for a patient in accordance with an embodiment of the invention is illustrated. Process 300 includes obtaining (310) patient brain data. As noted above, patient brain data can include structural and/or functional brain scans. In many embodiments, patient brain data includes both a structural MRI and a functional MRI scan. In various embodiments, multiple structural and/or functional MRI scans are included in the patient brain data which may have been captured at different times. MRI scans can be checked for quality. In various embodiments, scan quality is examined using commonly used fMRI quality control (QC) tools, and/or by matching whole brain connectivity structure against expected normative connectivity structure. Target identification processes for performing quality control using expected normative connectivity structure are discussed in further detail in a below section with reference to FIG. 4.

Process 300 further includes mapping (320) search and reference regions of interest (ROIs) onto the patient's brain. ROIs can be any brain structure, substructure, or group of structures of interest in the brain as decided by a user. Reference ROIs are ROIs that describe a region that the brain stimulation therapy should indirectly affect. In contrast, search ROIs describe regions in which individualized brain stimulation targets may reside. In this way, applying stimulation to an individualized brain stimulation target in a search ROI has an effect on the reference ROI. ROIs can be made up of one or more voxels depending on the size of the particular ROI. In some embodiments, ROIs may overlap. In numerous embodiments, a brain atlas is used to map ROIs onto a structural scan of the patient's brain. In various embodiments, target ROIs are indicated by applying a mask to the brain structure, where the mask flags desired target ROIs. In various embodiments, the mask can have different weight metrics for different desired target ROIs. ROIs can also be mapped onto functional scans. In various embodiments, a structural scan can be used as a template to align other functional scans. In various embodiments, multiple fMRI scans can be combined by integrating functional connectivity data to yield a "combined fMRI". In this way, multiple fMRIs taken of a patient with similar or identical protocols can be merged to yield a more complete picture of an individual's network connectivity.

fMRI signals (i.e. activity levels for a particular voxel or set of voxels over time) are extracted (330) from the ROIs. Voxels with poor signal quality can be excluded (335) and/or discarded. In numerous embodiments, poor quality signal can be caused due to various scanner limitations, scanning parameters and/or movement during the scanning process. In various embodiments, poor quality signals are detected by calculating voxel-level signal-to-noise ratio (SNR). By removing low quality signals from consideration, targeting accuracy can greatly increase. An individualized map of ROI parcellation is derived (340) from the extracted fMRI signals. The individualized map of ROI parcellations describes multiple parcels (or groups of adjacent voxels). Candidate parcels are derived from search ROIs, and constitute candidate targets for brain stimulation therapy. Reference parcels are derived from the reference ROI, and constitute areas of the reference ROI which will be impacted by the stimulation. Methods for deriving ROI parcellations in accordance with embodiments of the invention are discussed in further detail below with respect to FIG. 5.

Relationships between potential candidate and reference parcels are extracted (350) and a target score for potential candidate parcels are generated (360). In many embodiments, the functional connectivity between two parcels (a candidate and a reference) is measured and the target score is based on the strength of the functional connection. A target which has a stronger functional connectivity to a reference ROI (e.g. any parcel within the reference ROI), and therefore impacts functioning of the reference more strongly, can be given a higher target score. In many embodiments, other factors contribute to the score including (but not limited to) parcel depth, other functions of the parcel and/or surrounding brain structures, size, shape, and homogeneity of the parcel, fit to known/expected system/network-level connectivity profile, as well as numerous other factors can be considered as appropriate to the requirements of specific applications of embodiments of the invention. For example, a larger target may not have as strong functional connectivity to the reference, but is much larger and therefore easier to target with a specific brain stimulation device.

By way of additional example, a network connectivity score can be included which incorporates network-level expectations regarding which brain region to target can be included. If, in the literature, the field believes that a particular brain structure or network (i.e. set of structures) is involved with a particular condition, parcels that interact strongly with that brain structure/network may be weighted more heavily as potential targets. As noted above, the DLPFC is believed to be strongly linked to clinical depression and suicidal ideation, and therefore targets that strongly interact with that region may be more desirable based on current expectations.

As an example, in numerous embodiments, for each parcel, the difference between the functional connectivity to the DAN and the DMN can be calculated. Anticorrelation between the DAN and the DMN can be used as the network connectivity score, where a higher degree of anticorrelation suggests a stronger candidate parcel. In various embodiments, the difference between functional connectivity to the VAN and the DMN is calculated and used as a network connectivity score. In some embodiments, a weighted average of the network connectivity scores for different networks can be used as an overall network connectivity score, where the weights are based on the relevance of particular networks to a condition at issue. In various embodiments, the functional connectivities are calculated on a per-voxel basis and averaged to get an overall parcel score.

An individualized target parcel is then selected (370) from the group of candidate parcels based on the target scores. In many embodiments, the highest scored candidate parcel is selected. In many embodiments, the center for the target parcel is extracted (380) in order to more precisely determine TMS coil alignment. In many embodiments, the center is calculated by averaging the position of each voxel making up the target candidate.

While a particular method for generating an individualized target is illustrated in FIG. 3, as can be readily appreciated, any number of different modifications can be made without departing from the scope or spirit of the invention. For example, not every quality control step needs to be taken or every parameter considered for generating a network score as appropriate to the requirements of specific applications of embodiments of the invention. Further, different weights may be given to different parameters as to their relative importance in calculating a target score. Additional description of various steps of the above processes are found below.

Network Connectivity Quality Control

Patient brain data can include one or more fMRI scans, however there is rarely an immediate guarantee that the data is high quality (e.g. having a high SNR). Measurement noise and head movement are known causes of fMRI reliability limitation and are thus estimated and partially addressed as common practice during data preprocessing. However, in some cases, poor scan quality and or preprocessing errors are missed which can lead to deriving a target based of faulty brain functional connectivity structure. To prevent making clinical decisions based on faulty data, additional means are desirable.

Figure 4:
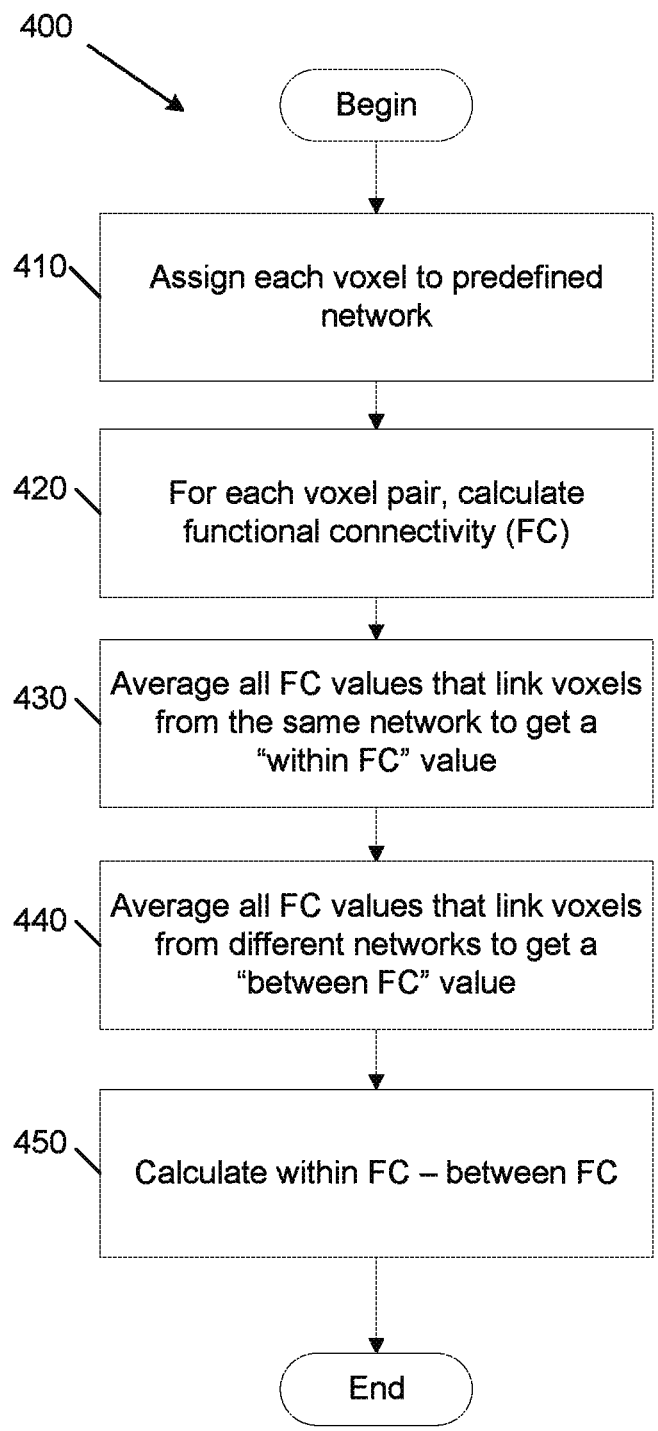
FIG. 4 is a flow chart illustrating a targeting process for evaluating expected network connectivity in accordance with an embodiment of the invention.

Under the probable and acceptable assumption of overall preservation in system-level organization of the human brain, matching measured whole-brain connectivity against expected normative connectivity can reduce errors from bad scans and, in some cases, provide a flag to medical professionals the presence of atypical brains for further manual scrutiny. In many embodiments, identified bad scans are discarded. Turning now to FIG. 4, a target identification process for measuring expected network connectivity in accordance with an embodiment of the invention is illustrated.

Process 400 includes assigning (410) each voxel to a predefined network. Many large-scale brain networks are known and have been mapped based on large samples of the population such as (but not limited to) the visual network (VIS), the sensorimotor network (SMN), the dorsal attention network (DAN), the ventral attention network (VAN), the limbic network, the frontoparietal control network (FPCN), and the default mode network (DMN). These networks can be overlaid onto an MRI of a patient such that each voxel is assigned to at least one network. For each voxel pair, a functional connectivity score (FC) can be calculated (420), where the FC represents the strength of the connectivity between the voxels in an fMRI (including a combined fMRI). All of the FC values that link voxels that are assigned to the same network are averaged (430) to yield a "within FC" value.

A "between FC" value is obtained by averaging (440) all FC values that link voxels from different networks. The between FC value is subtracted (450) from the within FC value to obtain a network fit for the voxel. While individual voxels may vary in their network association due to expected individual differences in brain function and structure, the average network fit across voxels (termed network quality control (QC) metric) is expected to remain positive (within FC>between FC) If the network QC metric is not significantly positive (mean between FC>=within FC), it is an indicator that there may be something either wrong with the scan, the preprocessing procedure or a significantly atypical structural issue occurring within the patient's brain. A statistical significance of network QC metric can be obtained by randomly permuting the data while considering voxel spatial positions and repeating the network QC estimation process. In this way, intake fMRIs can be cleared for quality. If an fMRI scan is flagged as having a poor overall network fit it can allow detailed inspection by a medical professional of the data and prevent deriving a target from faulty information.

While a particular method for QC control based on brain network connectivity is illustrated in accordance with an embodiment of the invention in FIG. 4, network connectivity can be used as a control using any of a number of different algorithms as appropriate to the requirements of specific applications of embodiments of the invention. Ensuring quality data can increase the accuracy of generated targets. A discussion of how to parcellate the brain into individualized ROIs is discussed further below.

ROI Parcellation

Figure 5:
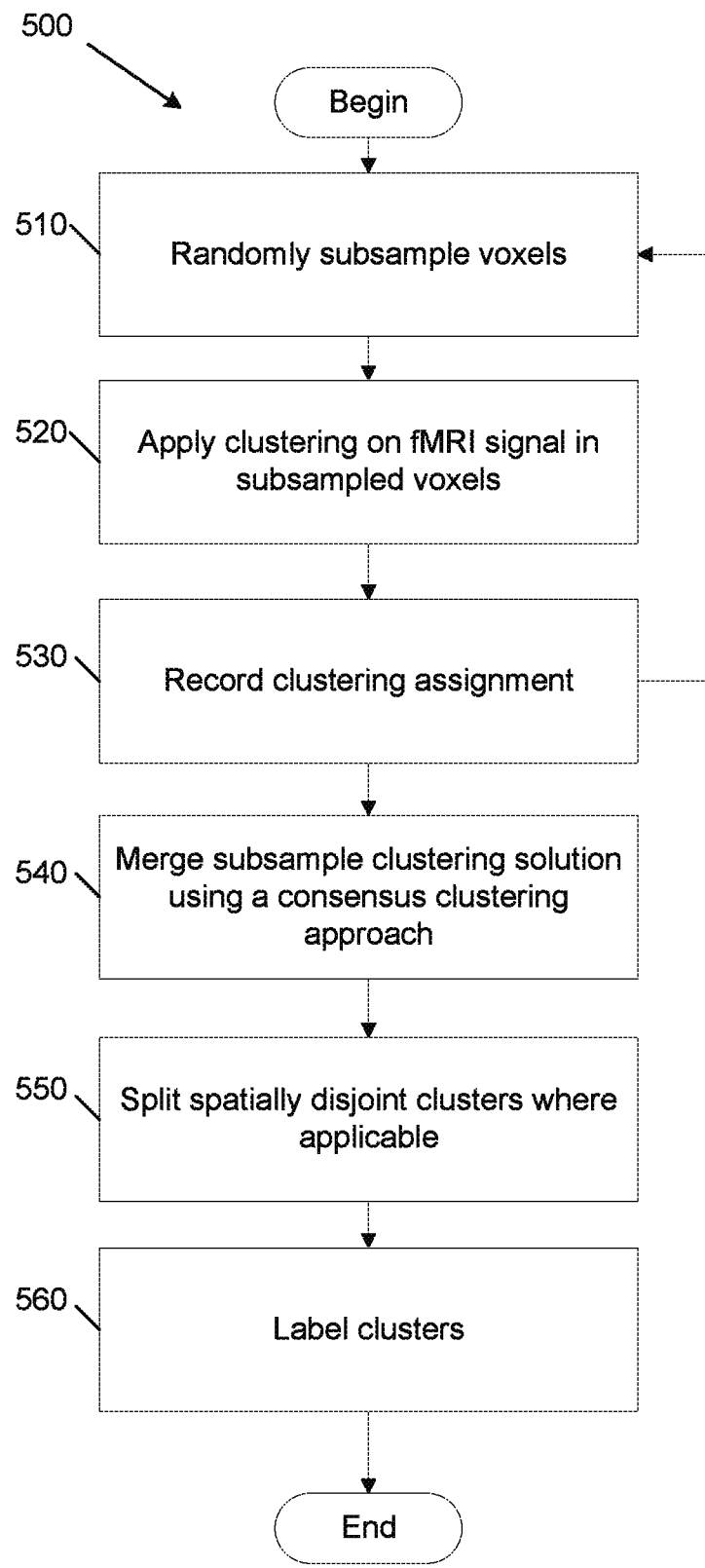
FIG. 5 is a flow chart illustrating a targeting process for deriving individualized ROI parcellations in accordance with an embodiment of the invention.

It is well known that while the overall structure of the human brain is relatively conserved across individuals, each person has idiosyncratic brain functionality and circuitry based on any number of factors both environmental and genetic. As such, merely dividing the brain based on a standardized model can yield inaccurate or insufficient results. While previous attempts have been made at parcellating the brain into ROIs, the particular methodologies used have often failed to robustly cluster voxels in an effective manner. Turning now to FIG. 5, a target identification process for deriving an individualized map of ROI parcellation in accordance with an embodiment of the invention is discussed.

Process 500 includes randomly subsampling (510) a percentage of all voxels. In many embodiments, the percentage is any number greater than 80%, however depending on the amount of data and compute available, this number can be less than 80%. The fMRI signals within the subsampled voxels are then clustered based on signal similarity (520). Any number of different clustering processes can be used including (but not limited to) agglomerative (hierarchical) clustering, Cluster Identification via Connectivity Kernels (CLICK) clustering, k-means clustering, and/or Spectral clustering. In some embodiments, clustering methods that incorporate spatial information (e.g. spatially constrained spectral clustering) can be used.

The clustering assignment is recorded (530) and a new random subsampling (510) is obtained. The process can be repeated many times to increase accuracy. In many embodiments, this process is repeated 100 or more times to ensure enough data, although fewer can suffice. The subsample clustering solutions are then merged (540). In many embodiments, they are merged using a consensus clustering approach. Any resulting spatially disjoint clusters can then be split (550) into sub-clusters. The clusters (and any sub-clusters) are then labeled (560) as parcels, either reference or search based on their locations within reference and search ROIs.

Figure 6:
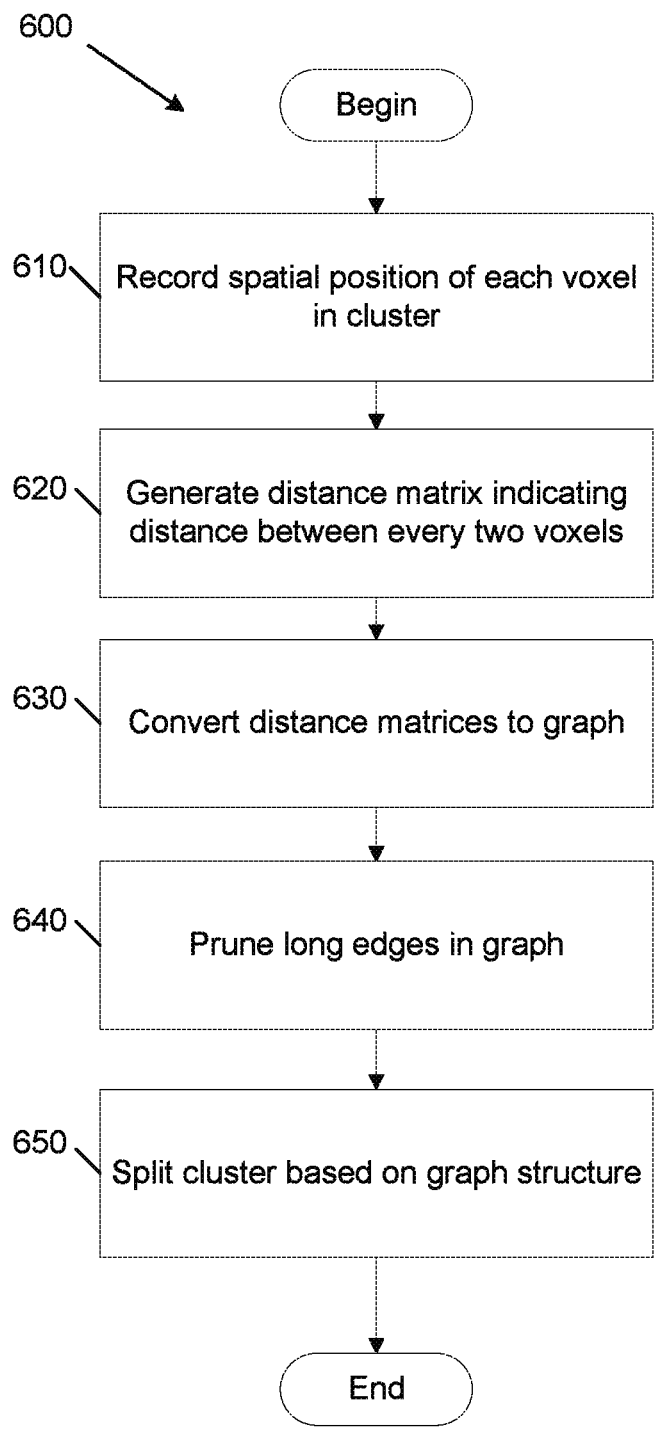
FIG. 6 is a flow chart illustrating a targeting process for splitting spatially disjoint clusters in accordance with an embodiment of the invention.

By repeatedly subsampling and clustering, noise in the neural signals can be accounted for and a more accurate picture of the individual's true brain connectivity can emerge. Furthermore, multiple fMRI scans can be run through this process and the resulting clusters can be integrated using consensus clustering. In this way, multiple fMRIs, including those taken on different days, can contribute to the overall dataset used for targeting. In various embodiments, spatially disjoint clusters can be avoided by using a spatially constrained clustering process. However, depending the requirements of specific applications of embodiments of the invention, it may be desirable to select a spatially unconstrained clustering process, which may yield spatially disjoint clusters. A target identification process for splitting spatially disjoint clusters in accordance with an embodiment of the invention is illustrated in FIG. 6.

Process 600 includes recording (610) the spatial position of each voxel in the spatially disjoint cluster. A distance matric indicating the physical distance between every two voxels is generated (620) which is then converted (630) into a graph representation. Long edges in the graph (edges that exceed a predefined threshold) are pruned (640) to yield a partially connected graph that is then split into connected sub-graphs (components) if such emerge. The set of voxels in each connected component can then be defined as a separate cluster (650).

In this way, a disjoint cluster can be split and separately used as potential candidate parcels for stimulation. In many embodiments, these disjoint clusters are problematic the "center" of a disjoint cluster may be outside any part of the disjoint cluster and nowhere near a viable target location.

Processes 300, 400, 500, and/or 600, and their variations, may be performed by a target identification system in order to provide a target parcel which then may be archived, stored for later use, transmitted to a neuronavigation device, used in further analysis, or combined with one or more other target parcels (for example, by union or intersection) to yield a composite target parcel. The target identification system may be distinct from, separate from, and/or integrated or partially integrated with a neuronavigation device. The target identification system may be implemented on a cloud computing platform, on a computing platform local to the site of treatment, on a computing platform incorporated into or part of a neuronavigation device, or any combination of such platforms.

Although specific methods of ROI parcellation are discussed above, many different methods can be implemented in accordance with many different embodiments of the invention, such as (but not limited to) those that use different specific clustering processes, and/or utilize different thresholds and parameters. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A targeted neuromodulation system, comprising:
a processor; and
a memory containing a targeting application, where the targeting application directs the processor to:
obtain patient brain data, where the patient brain data comprises a structural magnetic resonance imaging (sMRI) scan and at least one functional magnetic resonance imaging (fMRI) scan of a patient's brain, where the sMRI scan and the at least one fMRI scan each comprise a plurality of voxels;
assign a plurality of pairs of voxels in the fMRI scan to a large-scale brain network from a plurality of large-scale brain networks;
calculate a functional connectivity score for each pair of the plurality of pairs of voxels;
for each given voxel in the plurality of voxels:
calculate a first average functional connectivity score as the average of functional connectivity scores from given pairs of voxels in the plurality of pairs of voxels where the given voxel is in the given pair of voxels and where each voxel in the given pair of voxels is within the same large-scale brain network;
calculate a second average functional connectivity score as the average of functional connectivity scores from given pairs of voxels in the plurality of pairs of voxels where the given voxel is in the given pair of voxels and where each voxel in the given pair of voxels is from a different large-scale brain network; and
calculate a network fit for the given voxel by subtracting the second average functional connectivity score from the first functional connectivity score;
calculate a network quality control metric as an average of all the network fits;
identify the fMRI scan as passing a quality control test when the average network when the network quality control metric is above a threshold, and as failing the quality control test when the network quality control metric is below the threshold; and when the quality control test is passed:
map a reference region of interest (ROI) and at least one search ROI to the patient's brain using the sMRI scan and at least one fMRI scan:
where the reference ROI describes a region to be indirectly impacted via a brain stimulation therapy; and where the at least one search ROI describes at least one region to be directly targeted by the brain stimulation therapy;
derive an individualized map of ROI parcellation, where the individualized map of ROI parcellation describes the reference ROI as a plurality of reference parcels, and describes the at least one search ROI as a plurality of candidate parcels;
extract relationships between the plurality of candidate parcels and the plurality of reference parcels;
calculate a target score for candidate parcels in the plurality of candidate parcels based on the extracted relationships;
select a target parcel from the plurality of candidate parcels based on the target score; and
provide the target parcel; and
when the quality control test is failed, discard the fMRI scan.

2. The targeted neuromodulation system of claim 1, wherein the targeting application further directs the processor to provide the brain stimulation therapy to the target parcel in order to treat a mental condition of the patient.

3. The targeted neuromodulation system of claim 2, wherein the mental condition is major depressive disorder.

4. The targeted neuromodulation system of claim 2, wherein the brain stimulation therapy is selected from the group consisting of: transcranial magnetic stimulation; transcranial direct current stimulation; and electrical stimulation delivered via an implantable electrostimulator.

5. The targeted neuromodulation system of claim 1, wherein the targeting application further directs the processor to discard fMRI scans that deviate from expected whole brain network connectivity.

6. The targeted neuromodulation system of claim 1, wherein to derive the individualized map of ROI parcellation, the targeting application further directs the processor to:
randomly subsample voxels in the reference and at least one search ROIs;
cluster the subsample of voxels;
record a clustering assignment; and
label clusters in the clustering assignment as candidate parcels or reference parcels based on their location.

7. The targeted neuromodulation system of claim 1, wherein to derive the individualized map of ROI parcellation, the targeting application further directs the processor to:
randomly subsample voxels in the reference and at least one search ROIs as a first subsample of voxels;
cluster the first subsample of voxels;
record a first clustering assignment;
randomly subsample voxels in the reference and at least one search ROIs as a second subsample of voxels;
cluster the second subsample of voxels;
record a second clustering assignment;
merge the first clustering assignment and second clustering assignment using consensus clustering; and
label clusters in the merged clustering assignment as candidate parcels or reference parcels based on their location.

8. The targeted neuromodulation system of claim 1, wherein to derive the individualized map of ROI parcellation, the targeting application further directs the processor to split spatially disjoint clusters, where spatially disjoint clusters contain parcels which are clustered together but are not spatially contiguous.

9. The targeted neuromodulation system of claim 1, wherein the target score is calculated based on at least one factor from the group consisting of: parcel size, parcel depth, parcel shape, parcel homogeneity, functional connectivity strength to the reference ROI, and a network connectivity score.

10. The targeted neuromodulation system of claim 9, wherein the network connectivity score reflects anticorrelation between a default mode network and a dorsal attention network of the patient's brain.

11. The targeted neuromodulation system of claim 1 where the target parcel is transmitted from a cloud computing platform to a neuronavigation system.

12. A targeted neuromodulation method, comprising:
obtaining patient brain data, where the patient brain data comprises a structural magnetic resonance imaging (sMRI) scan and at least one functional magnetic resonance imaging (fMRI) scan of a patient's brain;

assigning a plurality of pairs of voxels in the fMRI scan a large-scale brain network from a plurality of large-scale brain networks;
calculating a functional connectivity score for each pair of the plurality of pairs of voxels;
for each given voxel in the plurality of voxels:
   calculating a first average functional connectivity score for as the average of functional connectivity scores from given pairs of voxels in the plurality of pairs of voxels where the given voxel is in the given pair of voxels and where each voxel in the given pair of voxels is within the same large-scale brain network;
   calculating a second average functional connectivity score as the average of functional connectivity scores from given pairs of voxels in the plurality of pairs of voxels where the given voxel is in the given pair of voxels and where each voxel in the given pair of voxels is from a different large-scale brain network; and
   calculating a network fit for the given voxel by subtracting the second average functional connectivity score from the first functional connectivity score;
calculating a network quality control metric as an average of all the network fits;
identifying the fMRI scan as passing a quality control test when the average network when the network quality control metric is above a threshold, and as failing the quality control test when the network quality control metric is below the threshold; and
when the quality control test is passed:
   mapping a reference region of interest (ROI) and at least one search ROI to the patient's brain using the sMRI scan and at least one fMRI scan:
   where the reference ROI describes a region to be indirectly impacted via a brain stimulation therapy; and
   where the at least one search ROI describes at least one region to be directly targeted by the brain stimulation therapy;
   deriving an individualized map of ROI parcellation, where the individualized map of ROI parcellation describes the reference ROI as a plurality of reference parcels, and describes the at least one search ROI as a plurality of candidate parcels;
   extracting relationships between the plurality of candidate parcels and the plurality of reference parcels;
   calculating a target score for candidate parcels in the plurality of candidate parcels based on the extracted relationships;
   selecting a target parcel from the plurality of candidate parcels based on the target score; and
   providing the target parcel; and
discarding the fMRI scan when the quality control test is failed.

13. The targeted neuromodulation method of claim 12, further comprising providing the brain stimulation therapy to the target parcel in order to treat the mental condition of the patient.

14. The targeted neuromodulation method of claim 13, wherein the mental condition is major depressive disorder.

15. The targeted neuromodulation method of claim 13, wherein the brain stimulation therapy is selected from the group consisting of: transcranial magnetic stimulation; transcranial direct current stimulation; and electrical stimulation delivered via an implantable electrostimulator.

16. The targeted neuromodulation method of claim 12, further comprising discarding fMRI scans that deviate from expected whole brain network connectivity.

17. The targeted neuromodulation method of claim 12, wherein deriving the individualized map of ROI parcellation comprises:
   randomly subsampling voxels in the reference and at least one search ROIs;
   clustering the subsample of voxels; and
   recording a clustering assignment;
   labeling clusters in the clustering assignment as candidate parcels or reference parcels based on their location.

18. The targeted neuromodulation method of claim 12, wherein deriving the individualized map of ROI parcellation comprises:
   randomly subsampling voxels in the reference and at least one search ROIs as a first subsample of voxels;
   clustering the first subsample of voxels;
   recording a first clustering assignment;
   randomly subsampling voxels in the reference and at least one search ROIs as a second subsample of voxels;
   clustering the second subsample of voxels;
   recording a second clustering assignment;
   merging the first clustering assignment and second clustering assignment using consensus clustering; and
   labeling clusters in the merged clustering assignment as candidate parcels or reference parcels based on their location.

19. The targeted neuromodulation method of claim 12, deriving the individualized map of ROI parcellation further comprises splitting spatially disjoint clusters.

20. The targeted neuromodulation method of claim 12, the target score is calculated based on at least one factor from the group consisting of: parcel size, parcel depth, parcel shape, parcel homogeneity, functional connectivity strength to the reference ROI, and a network connectivity score.

21. The targeted neuromodulation method of claim 12, wherein the network connectivity score reflects anticorrelation between a default mode network and a dorsal attention network of the patient's brain.

22. The targeted neuromodulation method of claim 12 where the target parcel is transmitted from a cloud computing platform to a neuronavigation system.

* * * * *